(12) United States Patent
Nakamura et al.

(10) Patent No.: US 7,728,119 B2
(45) Date of Patent: Jun. 1, 2010

(54) NUCLEOTIDE PRIMER SET AND NUCLEOTIDE PROBE FOR DETECTING GENOTYPE OF METHYLENE TETRAHYDROFOLATE REDUCTASE (MTHFR)

(75) Inventors: Naoko Nakamura, Kawasaki (JP); Keiko Ito, Kawasaki (JP); Masayoshi Takahashi, Tokyo (JP); Koji Hashimoto, Atsugi (JP); Nobuhiro Gemma, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/015,645

(22) Filed: Jan. 17, 2008

(65) Prior Publication Data

US 2008/0242554 A1 Oct. 2, 2008

(30) Foreign Application Priority Data

Mar. 28, 2007 (JP) ............... 2007-084288

(51) Int. Cl.
*C07H 21/02* (2006.01)
*C12Q 1/68* (2006.01)

(52) U.S. Cl. .......................... 536/23.1; 435/6
(58) Field of Classification Search .............. None
See application file for complete search history.

(56) References Cited

U.S. PATENT DOCUMENTS

| 6,410,278 | B1 | 6/2002 | Notomi et al. |
| 6,582,908 | B2 * | 6/2003 | Fodor et al. .......... 506/9 |
| 2007/0218464 | A1 | 9/2007 | Nakamura et al. |
| 2008/0242554 | A1 | 10/2008 | Nakamura et al. |

FOREIGN PATENT DOCUMENTS

| EP | 1 231 281 A1 | 8/2002 |
| EP | 1 837 408 A1 | 9/2007 |
| JP | 10-146183 | 6/1998 |
| JP | 3313358 | 5/2002 |
| JP | 2005-143492 | 6/2005 |
| WO | WO 02/24902 | 3/2002 |

OTHER PUBLICATIONS

New England Biolabs 1998/99 Catalog (NEB Catalog).*
Oligonucleotide Calculator (http://www.cnr.berkeley.edu/%7Ezimmer/oligoTMcalc.html; accessed on Apr. 4, 2009).*
K. Nagamine, et al., "Accelerated reaction by loop-mediated isothermal amplification using loop primers", Molecular and Cellular Probes, XP004471001, vol. 16, No. 3, Jun. 2002, pp. 223-229.
Meiju Ji, et al., "Microarray-based method for genotyping of functional single nucleotide polymorphisms using dual-color fluorescence hybridization", Mutation Research, XP002482382, vol. 548, No. 1-2, Apr. 14, 2004, pp. 97-105.
U.S. Appl. No. 11/624,814, filed Jan. 19, 2007, Nakamura et al.
U.S. Appl. No. 12/014,592, filed Jan. 15, 2008, Nakamura et al.
U.S. Appl. No. 12/341,295, filed Dec. 22, 2008, Nakamura et al.
Schildraut, Biopolymers, (1965), 3. pp. 195-208.
Freir et al, Proc. Natl. Acad. Sci, USA, (1986) 83, pp. 9373-9377.
Breslauer et al, Proc. Natl. Acad, Sci, USA, (1986) 83, pp. 3746-3750.
Jain, Mol. Diagn, (2005), 9(3), pp. 119-127.
U.S. Appl. No. 12/382,733, filed Mar. 23, 2009, Takahashi et al.
Guang Yin, et al., "Methylenetetrahydrofolate Reductase C677T and A1298C Polymorphisms and Colorectal Cancer: The Fukuoka Colorectal Cancer Study", Cancer Sci., vol. 95, No. 11, Nov. 2004, pp. 908-913.
Guang Yin, et al., "Methylenetetrahydrofolate Reductase C677T and A1298C Polymorphisms and Colorectal Cancer: The Fukuoka Colorectal Cancer Study", Cancer Sci., vol. 95, No. 11, Nov. 2004, pp. 908-913.

* cited by examiner

*Primary Examiner*—Christopher M. Babic
(74) *Attorney, Agent, or Firm*—Oblon, Spivak, McClelland, Maier & Neustadt, L.L.P.

(57) ABSTRACT

There is provided is a nucleotide primer set for LAMP amplification used for detecting genotypes of single-nucleotide polymorphisms C677T and A1298C of an MTHFR gene. There is also provided a nucleotide probe for detecting an amplification product amplified by the primer set according to the present invention. There is also provided a method of detecting the genotypes of the single-nucleotide polymorphisms C677T and A1298C in the MTHFR gene, by using the primer set according to the present invention.

16 Claims, 16 Drawing Sheets

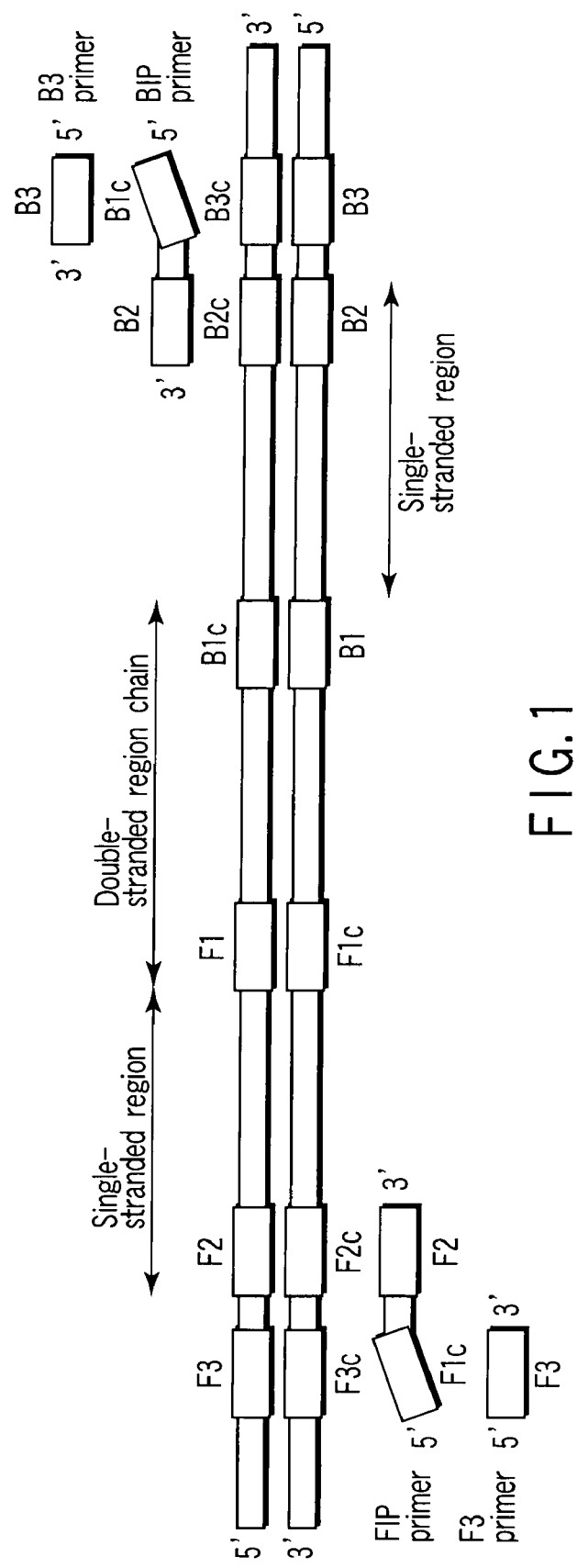
F I G. 1

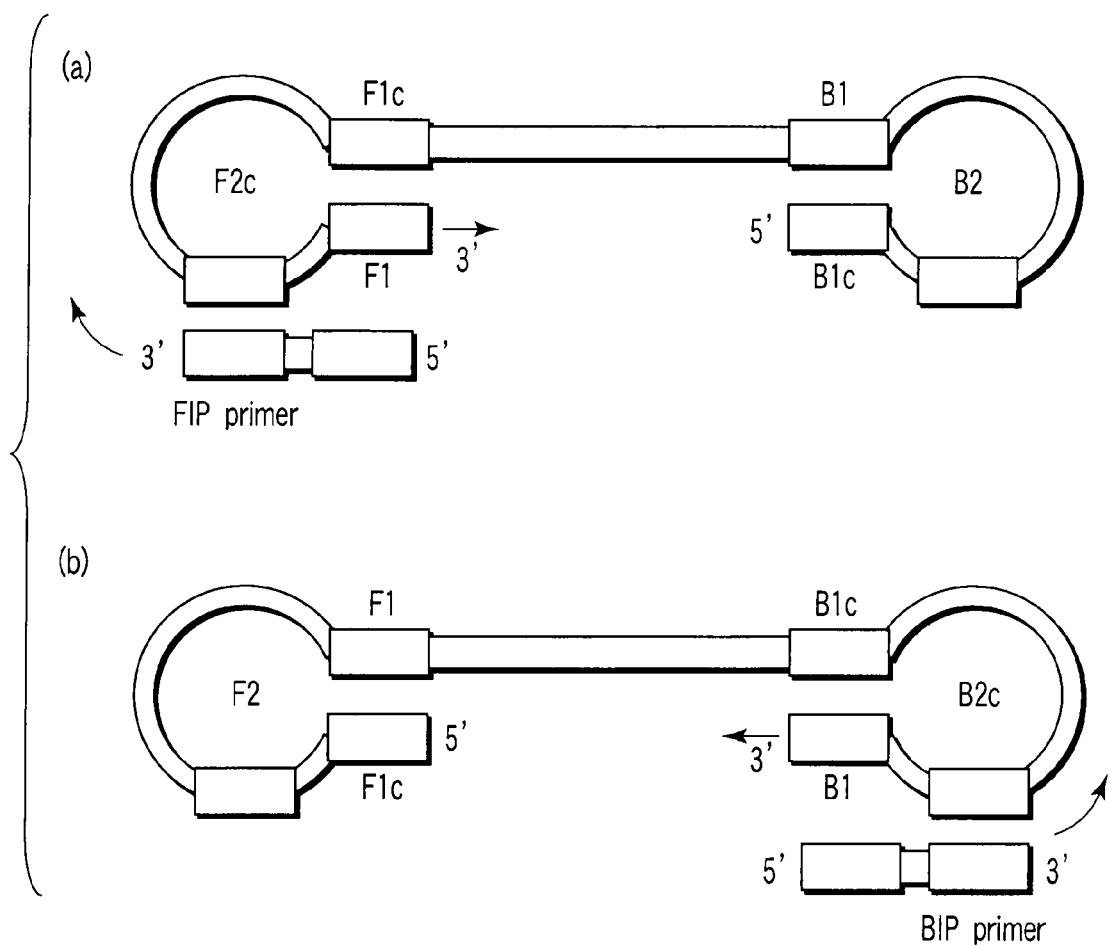
F I G. 2

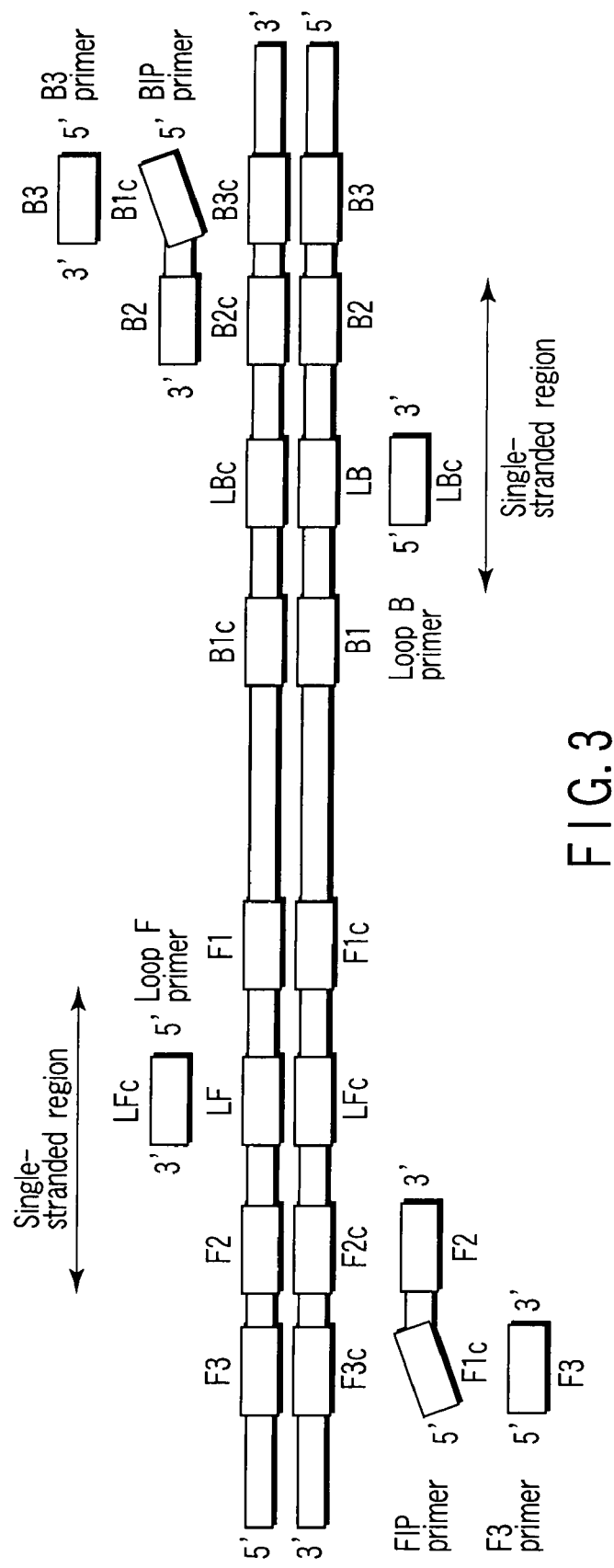
F I G. 3

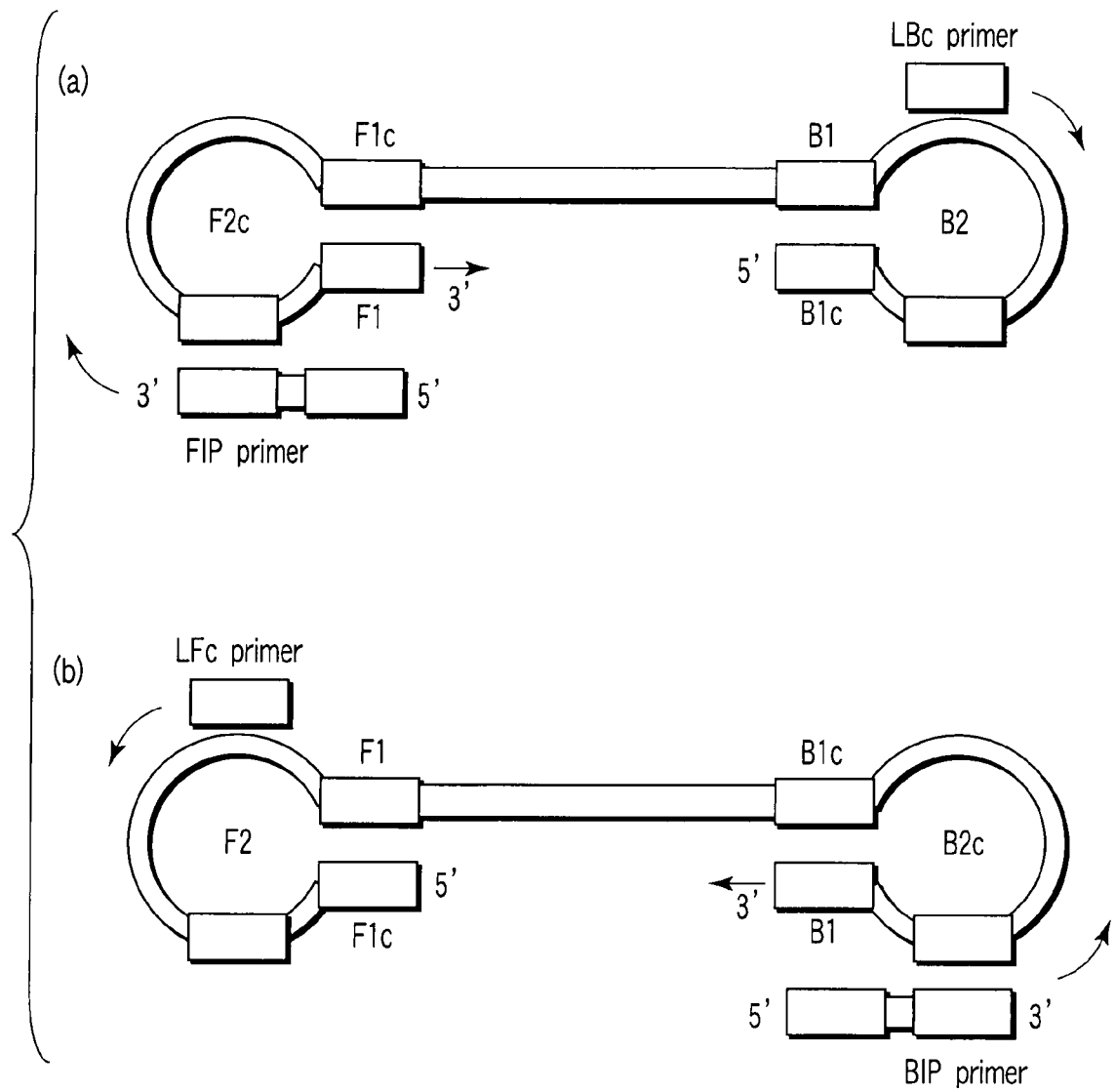
F I G. 4

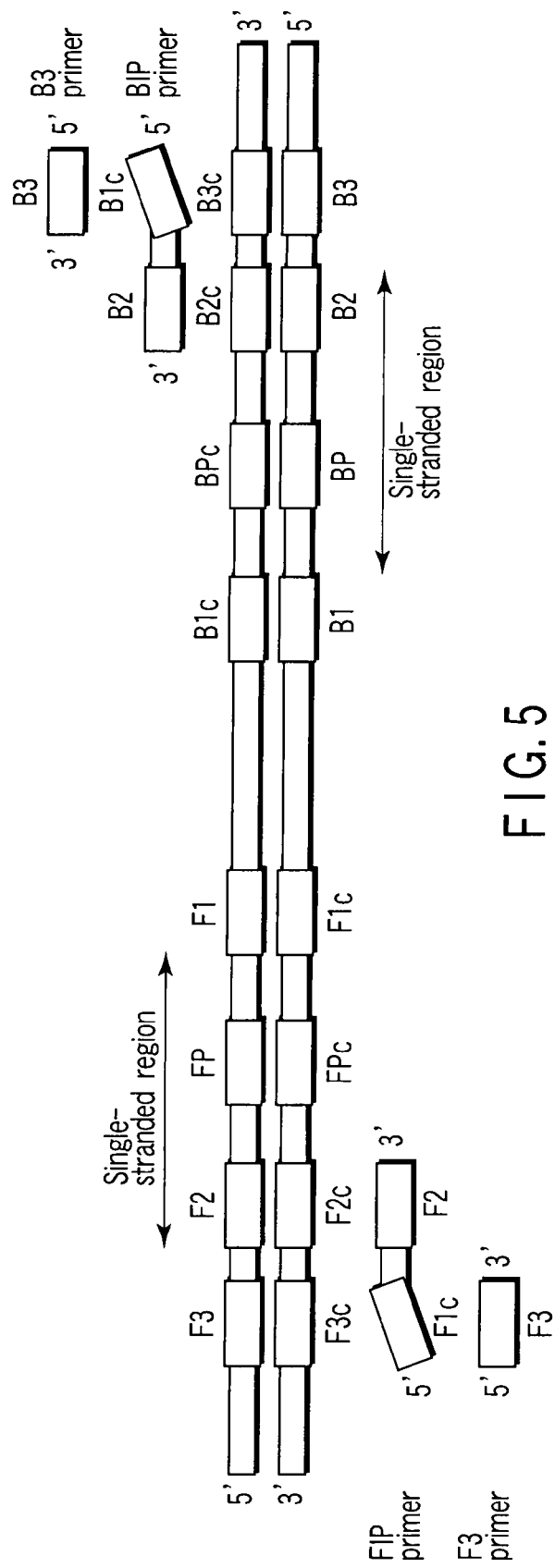
F I G. 5

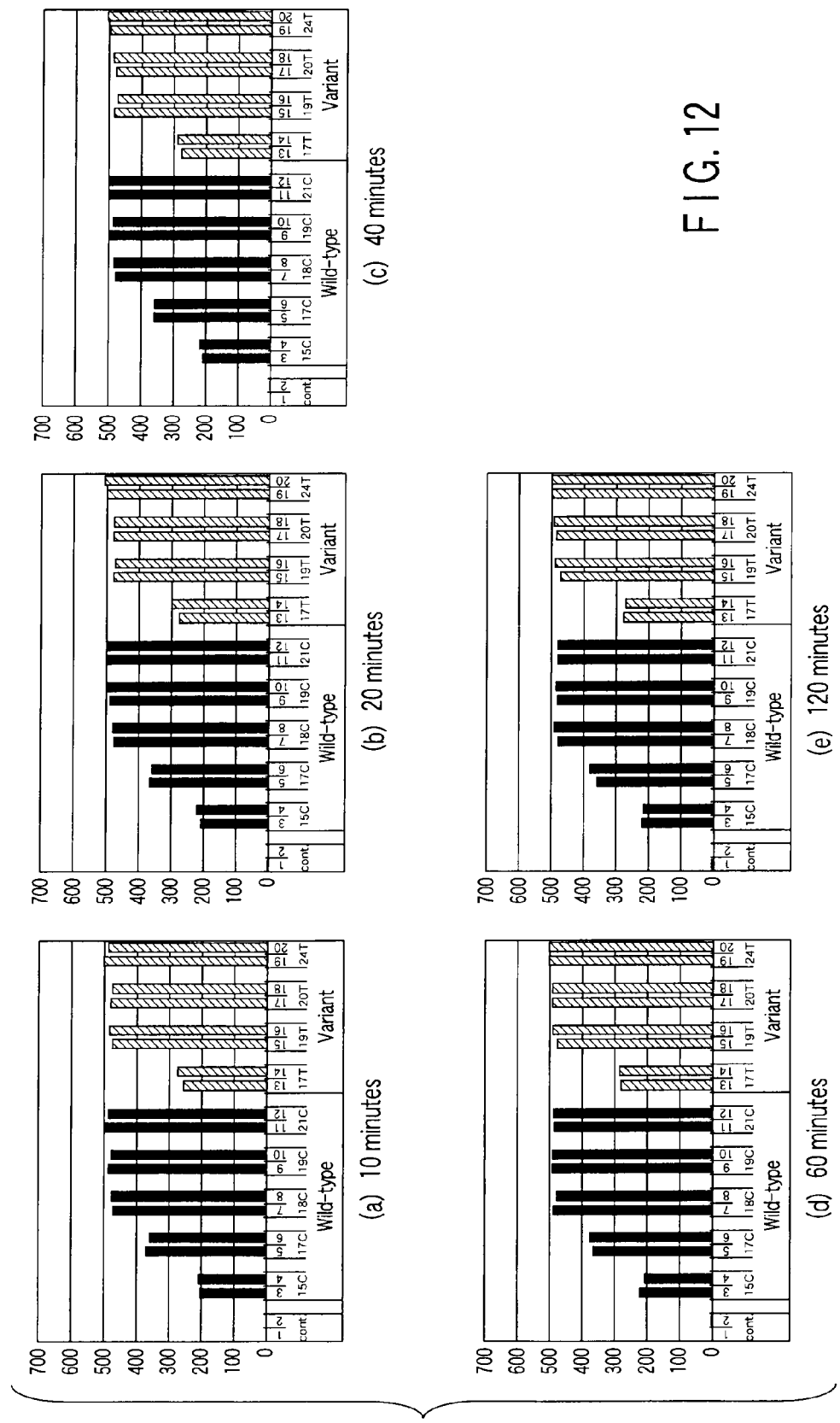
F I G. 12

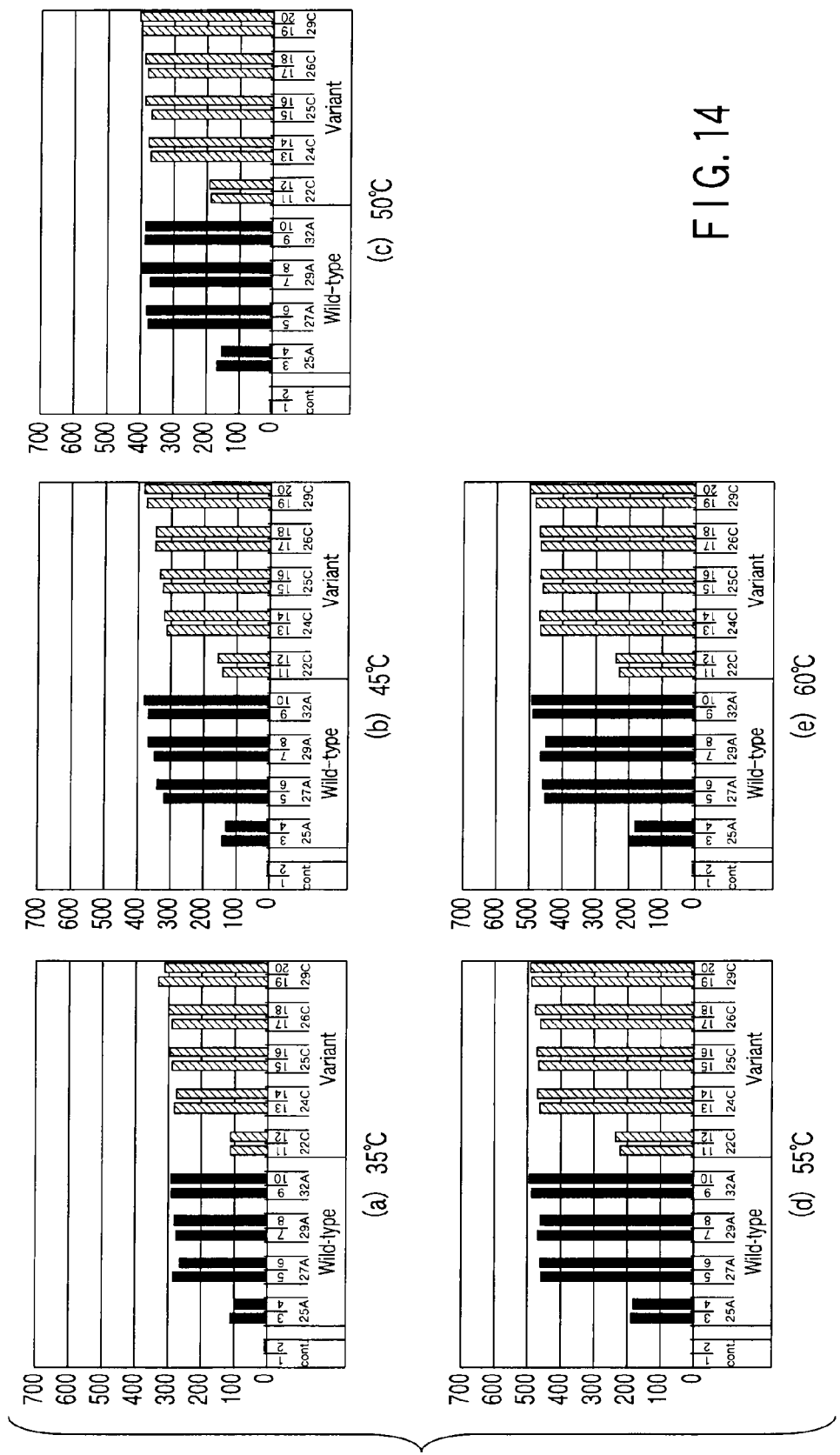
F I G. 14

NUCLEOTIDE PRIMER SET AND NUCLEOTIDE PROBE FOR DETECTING GENOTYPE OF METHYLENE TETRAHYDROFOLATE REDUCTASE (MTHFR)

CROSS-REFERENCE TO RELATED APPLICATIONS

This application is based upon and claims the benefit of priority from prior Japanese Patent Application No. 2007-084288, filed Mar. 28, 2007, the entire contents of which are incorporated herein by reference.

BACKGROUND OF THE INVENTION

1. Field of the Invention

The present invention relates to a nucleotide primer set and a detection probe for detecting a genotype in a single-nucleotide polymorphism of a methylene tetrahydrofolate reductase (MTHFR) gene.

2. Description of the Related Art

Methylene tetrahydrofolate reductase (MTHFR) is an enzyme involved in the metabolism of folic acid. It is essential for normal metabolism of homocysteine. The gene coding MTHFR has single-nucleotide polymorphisms C677T and A1298C. Mutation on the MTHFR gene alters its amino acid configuration and lowers its activity. Mutation on the MTHFR gene may induce hyperhomosysteinemia and is reported to increase the risk factor to arteriosclerotic diseases and colon cancer. In addition, correlation between the possibility of occurrence of side effects of methotrexate, which is an antirheumatic, and MTHFR gene polymorphism has been also reported.

Accordingly, it is valuable to analyze mutation of the MTHFR gene for prevention of medicinal side effects. It is also possible to perform pharmaceutical administration and treatment tailor-made to the patient, by determining the genotype of the MTHFR gene.

The single-nucleotide polymorphism is generally detected by amplifying a target nucleotide with the polymerase chain reaction (PCR) method and detecting wild-type and variant amplification products with a specific probe (see, the reference Jain K. K., Application of Amplicip. CYP450, Mol Diagn. 9, 119-27 [2005]). However, the PCR method has disadvantages such as complicated procedure of pretreatment including nucleotide extraction, demand for a complex temperature-regulating device such as a thermal cycler, and a longer reaction period of two hours or more. Amplification products by the PCR method are double-stranded chains, and thus, there is a problem in that the complementary chain degrades the detection sensitivity, while functioning as a competitor to the probe during detection. Various methods of converting the amplification product into a single-stranded chain, for example, by decomposing or separating a complementary chain by using an enzyme or magnetic beads, have been studied, but these methods also have a problem in that the operation is complicated and expensive.

BRIEF SUMMARY OF THE INVENTION

According to one aspect of the present invention, there is provided a nucleotide primer set for LAMP amplification, used for detecting a genotype of a single-nucleotide polymorphism C677T of an MTHFR gene, wherein when a target nucleotide has F3 region, F2 region and F1 region in turn from a 5' terminal and B3c region, B2c region and B1c region in turn from a 3' terminal, and when a primer set includes an FIP primer having a sequence identical with that of the F2 region in the 3' terminal side and a sequence complementary to the F1 region in the 5' terminal side, an F3 primer having a sequence identical with that of the F3 region, a BIP primer having a sequence complementary to the B2c region in the 3' terminal side and a sequence identical with that of the B1c region in the 5' terminal side, and a B3 primer having a sequence complementary to the B3c region, the primer set comprises: an FIP primer and a BIP primer selected from the primer sets 1 to 8 shown in Table 2; an F3 primer binding to a region within 60 bases from the 5' terminal of the F2 region of the target nucleotide; and a B3 primer binding to a region within 60 bases from the 3' terminal of the B2c region of the target nucleotide.

The primer sets 1 to 8 shown in Table 2 are as follows:
Primer set 1: FIP primer of SEQ ID No. 1 and BIP primer of SEQ ID No. 3,
Primer set 2: FIP primer of SEQ ID No. 1 and BIP primer of SEQ ID No. 4,
Primer set 3: FIP primer of SEQ ID No. 1 and BIP primer of SEQ ID No. 5,
Primer set 4: FIP primer of SEQ ID No. 1 and BIP primer of SEQ ID No. 6,
Primer set 5: FIP primer of SEQ ID No. 1 and BIP primer of SEQ ID No. 7,
Primer set 6: FIP primer of SEQ ID No. 9 and BIP primer of SEQ ID No. 3,
Primer set 7: FIP primer of SEQ ID No. 9 and BIP primer of SEQ ID No. 4,
Primer set 8: FIP primer of SEQ ID No. 9 and BIP primer of SEQ ID No. 5, According to another aspect of the present invention, there is provided a nucleotide primer set for LAMP amplification, used for detecting a genotype of a single-nucleotide polymorphism A1298C of an MTHFR gene, the primer set comprising: an FIP primer and a BIP primer selected from primer sets 1 to 5 shown in Table 3; an F3 primer binding to a region within 60 bases from the 5' terminal of the F2 region of the target nucleotide; and a B3 primer binding to a region within 60 bases from the 3' terminal of the B2c region of the target nucleotide.

The primer sets 1 to 5 shown in Table 3 are as follows:
Primer set 1: FIP primer of SEQ ID No. 14 and BIP primer of SEQ ID No. 16,
Primer set 2: FIP primer of SEQ ID No. 14 and BIP primer of SEQ ID No. 17,
Primer set 3: FIP primer of SEQ ID No. 14 and BIP primer of SEQ ID No. 19,
Primer set 4: FIP primer of SEQ ID No. 14 and BIP primer of SEQ ID No. 20,
Primer set 5: FIP primer of SEQ ID No. 14 and BIP primer of SEQ ID No. 21, According to another aspect of the present invention, there is provided a method of detecting a genotype of a single-nucleotide polymorphism C677T or A1298C of an MTHFR gene, comprising the steps of: obtaining an amplification product by amplifying a target nucleotide by using the nucleotide primer set; and measuring and comparing amounts of a wild-type amplification product and a variant amplification product contained in the amplification product.

Another aspect of the invention provides a nucleotide probe used for detecting amplification product obtained by amplifying a target nucleotide using the nucleotide primer set. In an aspect, wild-type nucleotide probe is complementary to wild-type amplification product and have a Tm value of 62 to 73° C., while the variant nucleotide probe is complementary to variant amplification product and have a Tm value of 61 to 71° C., and the single-nucleotide polymorphism C677T sites are located at positions 3 base or more inside from the terminal of the nucleotide probes respectively. In another aspect, wild-type nucleotide probe is complementary to wild-type amplification product and have a Tm value of 64 to 72° C., while the variant nucleotide probe is complementary to variant amplification product and have a Tm value of 63 to 73° C., and the single-nucleotide polymorphism A1298C sites are located at positions 3 bases or more inside from the terminal of the nucleotide probes respectively.

Another aspect of the invention provides a method of detecting the genotypes of the single-nucleotide polymorphisms C677T and A1298C of the MTHFR gene simultaneously.

The present invention also provides a nucleotide primer and a detection probe for detecting a genotype of a single-nucleotide polymorphism of MTHFR gene. It is thus possible to detect the genotype at the single-nucleotide polymorphism sites of C677T and A1298C of MTHFR gene easily and cost-effectively.

BRIEF DESCRIPTION OF THE SEVERAL VIEWS OF THE DRAWING

FIG. 1 is a schematic diagram showing a LAMP method;

FIG. 2 is a schematic diagram illustrating an intermediate product in the LAMP method and an annealing site of inner primers (FIP and BIP);

FIG. 3 is a schematic diagram illustrating the location of loop primers;

FIG. 4 is a schematic diagram illustrating the intermediate product in the LAMP method and the annealing site of the loop primers (LFc and LBc);

FIG. 5 is a schematic diagram illustrating the detection position of an amplification product;

FIG. 12 shows graphs showing test results 2 of a probe for detection of C677T;

FIG. 14 shows graphs showing test results 1 of a probe for detection of A1298C;

DETAILED DESCRIPTION OF THE INVENTION

Figure 6:
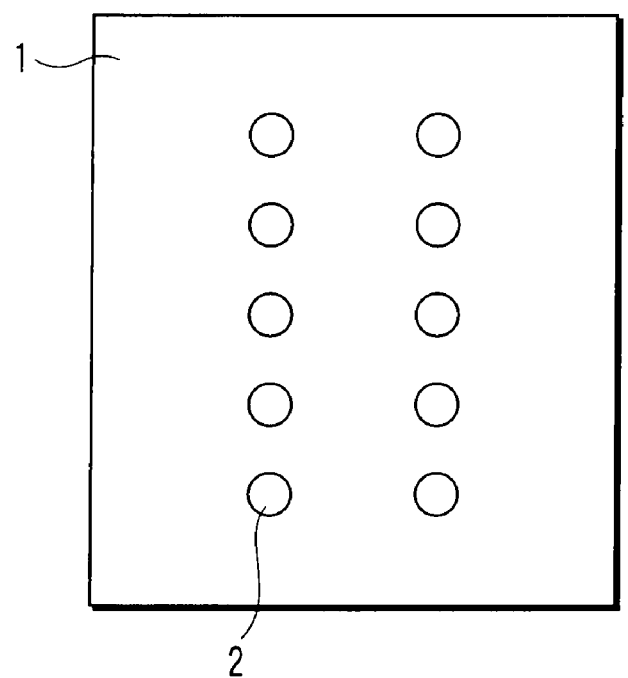
FIG. 6 is a planar schematic view of an embodiment of a probe-immobilized support.

The PCR method has been frequently used for detection of a single-nucleotide polymorphism, but the PCR method has the disadvantages described above. Thus in the present invention, the single-nucleotide polymorphism is detected by the loop-mediated isothermal amplification (LAMP) method, replacing the PCR method. In the LAMP method, a nucleotide is amplified under an isothermal condition at 60 to 65° C. The LAMP method has the advantage that it is possible to obtain amplification products in a shorter period in a greater amount than the PCR method. It is also reported that the reaction is less influenced by impurities in a sample. It is possible to amplify a target nucleotide easily by the LAMP method.

In one embodiment of the present invention, a target nucleotide is amplified by the LAMP method, and the amounts of the wild-type amplification products and variant amplification products in the amplification products obtained are respectively determined. When there are many wild-type amplification products, the genotype of the tested target nucleotide can be judged as a wild-type homo. On the contrary, when there are many variant amplification products, the target nucleotide can be judges as a variant homo. Alternatively, when there are almost the same amounts of the wild-type and variant amplification products, the target nucleotide can be judged as a heterozygous.

The amounts of the amplification products are determined, for example, by using a nucleotide probe. The nucleotide probes include one complementary to wild-type amplification products and one complementary to variant amplification products. Amplification products and the respective nucleotide probes are allowed to hybridize to each other, and the amounts of the amplification products bound to respective nucleotide probes are determined. It is possible to determine the genotype of the target nucleotide by comparing the amounts of the amplification products bound to a wild-type nucleotide probe and the amounts of the amplification products bound to a variant nucleotide probe.

<Summary of LAMP Method>

Hereinafter, the LAMP method will be described briefly. In the present specification, the nucleotide (including genomic DNA or the like) subjected to detection of a single-nucleotide polymorphism will be called analyte nucleotide. The region in the MTHFR gene amplified by the LAMP method will be called a target nucleotide. The products obtained by the LAMP method will be called amplification products. The solution containing human genomic DNAs will be called a sample solution.

In the LAMP method, the target nucleotide is designed to have F3 region, F2 region, and F1 region in turn from the 5' terminal and B3c region, B2c region, and B1c region in turn from the 3' terminal. The target nucleotides are amplified by using the four kinds of primers shown in FIG. 1. The regions F1c, F2c, F3c, B1, B2, and B3 are regions of the complementary chains respectively corresponding to the regions F1, F2, F3, B1c, B2c, and B3c.

The four kinds of primer used for amplification of the nucleotide in the LAMP method are (1) FIP primer having the sequence identical with the F2 region in the 3' terminal side and the sequence complementary to the F1 region in the 5' terminal side; (2) F3 primer having the sequence identical with the F3 region; (3) BIP primer having the sequence complementary to the B2c region in the 3' terminal side and the sequence identical with the B1c region in the 5' terminal side; and (4) B3 primer having the sequence complementary to the B3c region. Generally, FIP and BIP primers are called inner primers, while F3 and B3 primers are called outer primers.

LAMP amplification by using the four kinds of primers gives intermediate products having the dumbbell structure shown in FIG. 2. FIP and BIP primers bind to F2c region and B2c region in single-stranded loops, and extending reaction proceeds from the 3' terminal of the each primer and the 3' terminal of the intermediate product itself. See Japanese Patent No. 3313358 for details.

It is possible to shorten the amplification period by using a primer called loop primer optionally in the LAMP method. In such a case, as shown in FIG. 3, a LF region is designed in the region from F2 region to F1 region and a LBc region is designed in the region from B2c region to B1c region. These regions are called loop primer region. In addition to the four kinds of primers, a loop primer LFc having the sequence complementary to the region LF and a loop primer LBc having the sequence identical with the region LBc are used. See WO2002/024902 for details. These loop primers LFc and LBc may be used simultaneously, or alternatively, only one of them may be used. The loop primers are annealed to a loop different from the loop to which FIT and BIP primers are annealed, as shown in FIG. 4, giving additional synthetic origins and thus accelerating amplification.

<Detection of LAMP Amplification Products; Nucleotide Probe>

For detection of a single-nucleotide polymorphism, the polymorphic site to be detected is located in the FP region or BPc region shown in FIG. 5. As shown in FIG. 5, the region from F2 region to F1 region is a part that becomes single stranded in the amplification product. Similarly, the region from B2c region to B1c region is also a part that becomes single-stranded in the amplification product. It is possible to make the detection by nucleotide probe easier, by locating the polymorphic site to be detected in a single-stranded part.

The nucleotide probe is designed to bind to the FP region or BPc region containing the polymorphic site. Thus, the nucleotide probe has a sequence complementary to that of the region containing polymorphic site among FP region or BPc region.

FPc region complementary to regions FP and BP region complementary to regions BPc is also present in the amplification products. Accordingly, it is possible to use the FPc region and BP region for detection.

In the present specification, nucleotide probes containing sequences complementary to that of wild-type amplification products are called wild-type nucleotide probes, while the nucleotide probes containing the sequences complementary to that of variant amplification products are called variant nucleotide probes.

The nucleotide probe may be consisted of, but is not limited to, DNA, RNA, PNA, LNA, nucleotide having a methyl phosphonate skeleton, or other synthetic nucleotide chain. For immobilization on a support, the terminal thereof may be modified with a reactive functional group such as amino, carboxyl, hydroxyl, thiol, or sulfonyl group. A spacer may be introduced between the functional group and the nucleotide. The spacer may have, for example, an alkane skeleton, an ethylene glycol skeleton, or the like.

<Nucleotide Probe-Immobilized Support>

The nucleotide probe may be used, for example, as it is immobilized on a support. The nucleotide probe-immobilized support may be used in a known apparatus such as so-called DNA chip and DNA microarray.

An embodiment of the probe-immobilized support is shown in FIG. 6. The probe is immobilized in an immobilization region 2 of a support 1. The support 1 may be prepared with a silicon substrate, but is not limited thereto. The probe may be immobilized by known means. Only one kind of probe may be immobilized on a support, or different kinds of probe may be immobilized on a support, the location and the number thereof may be modified as needed by those who are skilled in the art. As will be described below, a probe-immobilized support according to the present embodiment may be used for fluorescent detection of a probe.

Figure 7:
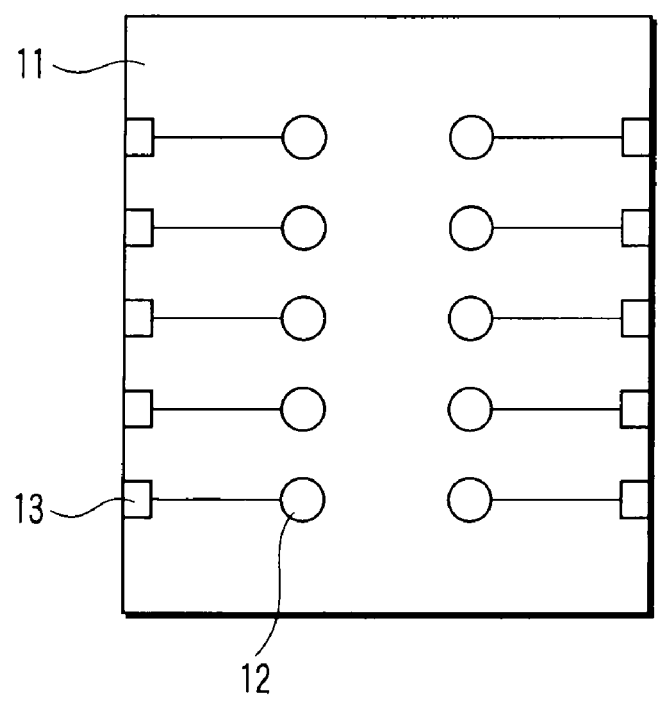
FIG. 7 is a planar schematic view illustrating an embodiment of the probe-immobilized support.

A schematic view of the probe-immobilized support in another embodiment is shown in FIG. 7. In the present embodiment, electrodes 12 are formed on a support 11. The probe is immobilized on the electrode 12. Each electrode 12 is connected to a pad 13 for extracting electrical information. The support 11 may be prepared, for example, from a silicon substrate, but is not limited thereto. Production of electrode and immobilization of probe may be performed by any known means. The electrode can be made of any material which include, but not limited to, single metals such as gold, gold alloy, silver, platinum, mercury, nickel, palladium, silicon, germanium, gallium and tungsten, alloys thereof, carbons such as graphite and glassy carbon, and the oxides or compounds thereof.

The immobilization support shown in FIG. 7 has 10 electrodes, but the number of the electrodes formed on a single support is not limited thereto and may be modified optionally. The positional pattern of the electrodes is also not limited to that shown in the figure, and may be modified as needed by those who are skilled in the art. Reference electrodes and counter electrodes may be formed as needed on the support 1. As will be described below, a probe-immobilized support according to this embodiment may be used when probe is detected electrochemically.

<Hybridization of Nucleotide Probe with Amplification Product>

The amplification products are hybridized to the nucleotide probe under a suitable condition. The suitable condition varies according to the kind and structure of the amplification products, the kind of nucleotide contained in the sequence to be detected, and the kind of nucleotide probe. Specifically, the hybridization is performed in a buffer solution at an ionic strength in the range of 0.01 to 5 and at a pH in the range of 5 to 10. Dextran sulfate which is a hybridization accelerator, salmon sperm DNA, bovine thymic DNA, EDTA, a surfactant, and the like may be added to the reaction solution. The reaction temperature is, for example, in the range of 10 to 90° C., and the reaction mixture may be stirred or shaken for improvement in reaction efficiency. After reaction, a buffer solution for example at an ionic strength in the range of 0.01 to 5 and at a pH in the range of 5 to 10 may be used for washing.

<Detection Method>

Hybridization between the probe immobilized on the support and the amplification products gives double-strand nucleotides. The double-strand nucleotides can be detected electrochemically or by fluorescence.

(a) Current Detection System

Electrochemical detection of the double-strand nucleotide will be described below. The method uses a double-stranded chain-recognizing compound that recognizes a double-strand nucleotide specifically. Examples of the double-stranded chain-recognizing compounds include, but are not limited to, Hoechst 33258, acridine orange, quinacrine, daunomycin, metallointercalators, bisintercalators such as bisacridine, tris-intercalators, and polyintercalators. These substances may be modified with an electrochemically active metal complex such as ferrocene or viologen.

The concentration of the double-stranded chain-recognizing compound may vary according to its kind, but generally, it is used at a concentration range of 1 ng/mL to 1 mg/mL. In this case, a buffer solution at an ionic strength in the range of 0.001 to 5 and at a pH in the range of 5 to 10 is used preferably.

A double-stranded chain-recognizing compound is added to the reaction solution during or after hybridization reaction. The double-stranded chain-recognizing compound binds to double-strand nucleotides, if formed by hybridization. For example, it is possible to measure the reaction current derived from the double-stranded chain-recognizing compound, by applying an electric potential higher than that causing electrochemical reaction of the double-stranded chain-recognizing compound. In this case, the electric potential may be applied at a constant velocity, or applied in the pulse shape or at the constant voltage. The current and voltage may be controlled during measurement by using a device such as potentiostat, digital multimeter, or function generator. For example, the known electrochemical detecting means disclosed in JP-A 10-146183 (KOKAI) is used preferably.

(b) Fluorescent Detection Method

The method of detecting double-strand nucleotide by fluorescence will be described below. The primer is previously labelled with a fluorescently active substance. Alternatively, it is detected with a secondary probe labelled with a fluorescently active substance. A secondary probe with multiple labels may be used. Examples of the fluorescently active substance include, but are not limited to, fluorescent colorants such as FITC, Cy3, Cy5, and rhodamine. The fluorescent material is detected, for example, with a fluorescence detector. A detector suitable for the kind of label is used for detection of labeled sequence to be detected or secondary probe.

<Selection of Nucleotide Primer>

Figure 8:
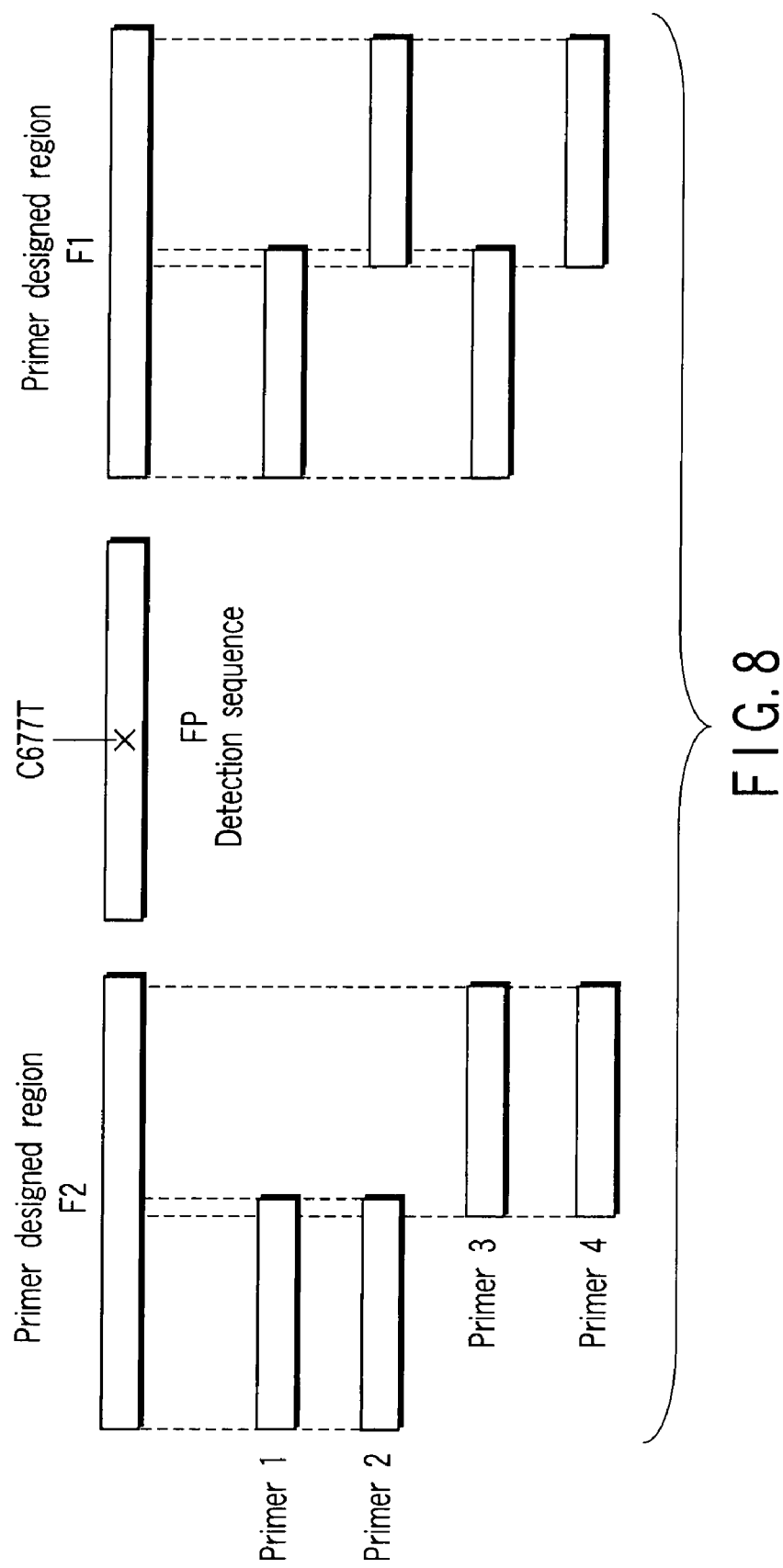
FIG. 8 is a schematic diagram showing the location of FIP primer.

FIG. 8 is a schematic diagram showing nucleotide primers, when a single-nucleotide polymorphism C677T is located in the region between F2 and F1, i.e., FP region. The FIP primer has the same sequence as the F2 region and the sequence complementary to that of the F1 region. Various kinds of primers may be designed, as long as the F2 region and F1 region is positioned at places holding C677T inside.

However, studies by the inventors have revealed that the amplification efficiency by the LAMP method varies according to the kind of primer. For example, amplification is performed by using primer one of the four kinds of primers shown in FIG. 8, and common three primers (BIP, F3, and B3 primers). As a result, the sample with primer 1 is not amplified even after a sufficient period, for example after 2 hours. The sample with primer 2 is amplified after approximately 1 hour, but non-specific amplification of primers is occurred. The sample with primer 3 does not cause non-specific amplification of primers, but requires an amplification period of 1.5 to 2 hours. The sample with primer 4 causes no non-specific amplification of primers and completes amplification within 1 hour. In this case, the primers preferable for amplification are the primers 3 and 4, and the best primer is the primer 4. Thus, it is superior primer that is higher in amplification efficiency, allows amplification in a short period, and causes no non-specific amplification.

For detection of amplification products with a nucleotide probe, the amplification product preferably hybridizes with the nucleotide probe at a high efficiency. Accordingly, hybridization efficiency of the amplification products is also considered in evaluating the primer.

As for the other inner primer having no single-nucleotide polymorphism site, it is preferably designed to the region where the length from F2 to B2 is preferably 450 bp or less, more preferably 350 bp or less. The length of the single-stranded region, i.e., region from F2 to F1, or the region from B2c to B1c, is preferably 100 bp or less, more preferably 70 bp or less.

Non-specific amplification among primers is a phenomenon often found in the LAMP reaction. The FIP primer, which contains the F1c region and F2 region, is often a long-chain nucleotide. Similarly, the BIP primer, which contains the B1c region and B2 region, is often a long-chain nucleotide. Thus, among FIP primers, among BIP primers, or FIP and BIP primers may be entangled with each other, frequently allowing amplification of which template is primer. The possibility of non-specific reaction is higher in the LAMP reaction than in the PCR reaction, because the reaction solution contains the F3 and B3 primers and additionally LFc and LBc primers in some cases. Such non-specific reaction leads to decrease in the amount of desirable LAMP products obtained by using the analyte nucleotide as the template.

If non-specific reaction occurs in a negative control reaction solution containing no added analyte nucleotide, it is not possible to determine whether the white precipitate of pyrophosphoric acid and Mg released along with progress of amplification is caused by non-specific amplification or by contamination. Accordingly, it is important to eliminate the primers possibly causing non-specific amplification.

Accordingly, the inventors have conducted tests for selection of the nucleotide primer most preferable for amplification of a single-nucleotide polymorphism C677T of the MTHFR gene, and also for amplification of a single-nucleotide polymorphism A1299C.

[Test 1: Primer for C677T]

Amplification was performed at 63° C. for 1 hour or 2 hours, by using 14 kinds of nucleotide primer sets containing MTHFR C677T polymorphic site in the FP region. The composition of the reaction solution is shown in Table 1. The template DNA used was a human genome. For examination of the presence or absence of contamination and non-specific amplification, a negative control containing sterilized ultrapure water instead of the human genome was prepared in all sets. After amplification reaction, amplification products were identified by 3% agarose electrophoresis.

The nucleotide primer sets used are shown in Table 2.

TABLE 1

| LAMP reaction composition | |
|---|---|
| Bst DNA Polymerase | 1 μL |
| 2 × Buffer | 12.5 μL |
| Tris · HCl pH 8.0 40 mM | |
| KCl 20 mM | |
| MgSO$_4$ 16 mM | |
| (NH$_4$)$_2$SO$_4$ 20 mM | |
| Tween20 0.2% | |
| Betaine 1.6 M | |
| dNTP 2.8 mM | |
| F3 primer (10 μM) | 0.5 μL |
| B3 primer (10 μM) | 0.5 μL |
| FIP primer (40 μM) | 1 μL |
| BIP primer (40 μM) | 1 μL |
| LFc primer (20 μM) | 1 μL |
| Human genome (30 ng/μL) | 1 μL |
| Sterilized ultrapure water | 6.5 μL |
| Total | 25 μL |

TABLE 2

Primer set designed to have C677T in FP and FPc regions

| Primer set | SEQ ID No. | Name | Sequence | 1-hour amplification | 2-hour amplification | Non-specific amplification |
|---|---|---|---|---|---|---|
| 9 | 1 | FIP-1 | TCAGCCTCAAAGAAAAGCTGAGGCTGACCTGAAGCACT | X | X | Not-occurred |
|   | 2 | BIP-1 | CTTCCGCTTTGTGAAGGCATGCCCCTCACCTGGATGGGAAA |   |   |   |
| 1 | 1 | FIP-1 | TCAGCCTCAAAGAAAAGCTGAGGCTGACCTGAAGCACT | X | ○ | Not-occurred |
|   | 3 | BIP-2 | CACATTCTTCCGCTTTGTGAAGGCCCCTCACCTGGATGGGAAA |   |   |   |
| 2 | 1 | FIP-1 | TCAGCCTCAAAGAAAAGCTGAGGCTGACCTGAAGCACT | ○ | ○ | Not-occurred |
|   | 4 | BIP-3 | CAGGAGAGCCCATAAGCTCCCTTCAGCACTCCACCCAGAG |   |   |   |
| 3 | 1 | FIP-1 | TCAGCCTCAAAGAAAAGCTGAGGCTGACCTGAAGCACT | ○ | ○ | Not-occurred |
|   | 5 | BIP-4 | GAGAGCCCATAAGCTCCCTCCATCAGCACTCCACCCAGAG |   |   |   |
| 4 | 1 | FIP-1 | TCAGCCTCAAAGAAAAGCTGAGGCTGACCTGAAGCACT | ○ | ○ | Not-occurred |
|   | 6 | BIP-5 | GAGAGCCCATAAGCTCCCTCCAACTCAGCACTCCACCCAG |   |   |   |
| 5 | 1 | FIP-1 | TCAGCCTCAAAGAAAAGCTGAGGCTGACCTGAAGCACT | ○ | ○ | Not-occurred |
|   | 7 | BIP-6 | AGCCCATAAGCTCCCTCCACCACTCAGCACTCCACCCAG |   |   |   |
| 10 | 1 | FIP-1 | TCAGCCTCAAAGAAAAGCTGAGGCTGACCTGAAGCACT | X | X | Not-occurred |
|   | 8 | BIP-7 | CCATCGTCCCCGGGAGGAGCTTATGGGCTCTCCT |   |   |   |
| 11 | 9 | FIP-2 | GCCTCAAAGAAAAGCTGCGTGTGAAGCACTTGAAGGAGAAGG | X | X | Not-occurred |
|   | 2 | BIP-1 | CTTCCGCTTTGTGAAGGCATGCCCCTCACCTGGATGGGAAA |   |   |   |
| 6 | 9 | FIP-2 | GCCTCAAAGAAAAGCTGCGTGTGAAGCACTTGAAGGAGAAGG | X | ○ | Not-occurred |
|   | 3 | BIP-2 | CACATTCTTCCGCTTTGTGAAGGCCCCTCACCTGGATGGGAAA |   |   |   |
| 7 | 9 | FIP-2 | GCCTCAAAGAAAAGCTGCGTGTGAAGCACTTGAAGGAGAAGG | ○ | ○ | Not-occurred |
|   | 4 | BIP-3 | CAGGAGAGCCCATAAGCTCCCTTCAGCACTCCACCCAGAG |   |   |   |
| 8 | 9 | FIP-2 | GCCTCAAAGAAAAGCTGCGTGTGAAGCACTTGAAGGAGAAGG | ○ | ○ | Not-occurred |
|   | 5 | BIP-4 | GAGAGCCCATAAGCTCCCTCCATCAGCACTCCACCCAGAG |   |   |   |
| 12 | 9 | FIP-2 | GCCTCAAAGAAAAGCTGCGTGTGAAGCACTTGAAGGAGAAGG | ○ | ○ | Occurred |
|   | 6 | BIP-5 | GAGAGCCCATAAGCTCCCTCCAACTCAGCACTCCACCCAG |   |   |   |
| 13 | 9 | FIP-2 | GCCTCAAAGAAAAGCTGCGTGTGAAGCACTTGAAGGAGAAGG | ○ | ○ | Occurred |
|   | 7 | BIP-6 | AGCCCATAAGCTCCCTCCACCACTCAGCACTCCACCCAG |   |   |   |
| 14 | 9 | FIP-2 | GCCTCAAAGAAAAGCTGCGTGTGAAGCACTTGAAGGAGAAGG | X | X | Not-occurred |
|   | 8 | BIP-7 | CCATCGTCCCCGGGAGGAGCTTATGGGCTCTCCT |   |   |   |
|   | 10 | F3 | GTTACCCCAAAGGCCACC |   |   |   |
|   | 11 | B3-1 | GGAGCTTATGGGCTCTCCT |   |   |   |
|   | 12 | B3-2 | TCTGGGAAGAACTCAGCGA |   |   |   |
|   | 13 | B3-3 | TCAGCACTCCACCCAGAG |   |   |   |
|   | 27 | LBc | CCGCACCGTCCTCGCACAGGC |   |   |   |

The nucleotide of SEQ ID No. 10 was used as the F3 primer in all sets. The nucleotide of SEQ ID No. 11 was used as the B3 primer in primer sets 1, 6, 9, and 11; the nucleotide of SEQ ID No. 12, in primer sets 2, 3, 4, 5, 7, 8, 12, and 13; and the nucleotide of SEQ ID No. 13, in primer sets 10 and 14.

[Test 1: Results]

Figure 9:
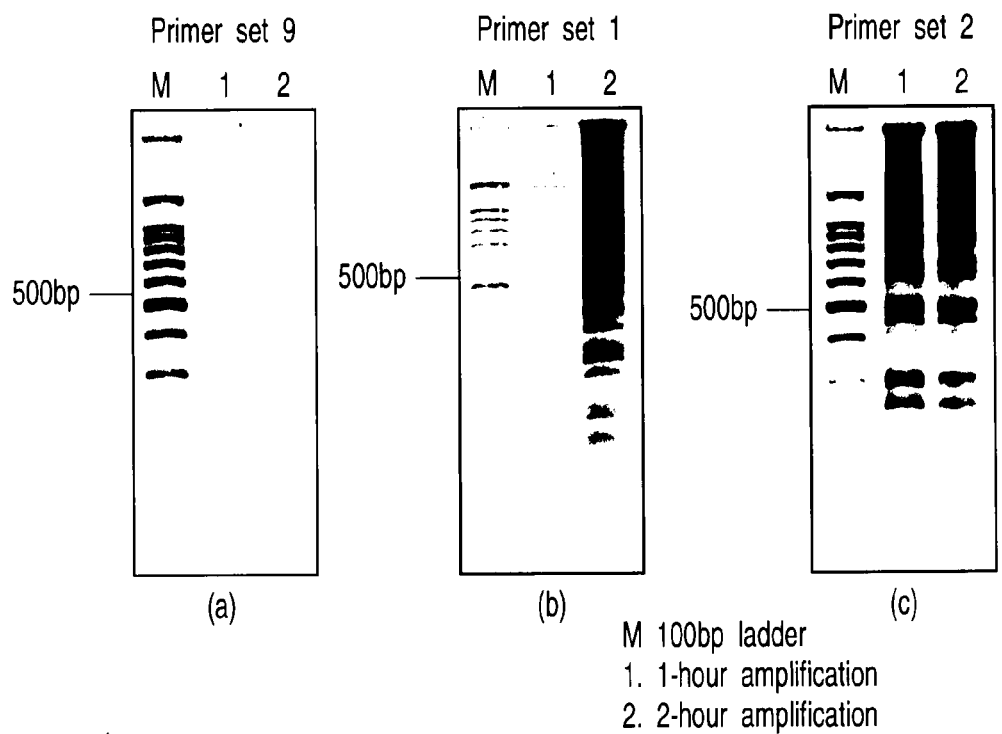
FIG. 9 shows electrophoretograms of the amplification products obtained by using the primer set.

The reaction products after amplification for 1 hour or for 2 hours with the primer sets 1, 2, and 9 were subjected to electrophoresis. The results are summarized in FIG. 9. There was no amplification product obtained even after 2 hours with the primer set 9. There was no amplification product after reaction for 1 hour with the primer set 1. There were sufficient amounts of amplification products obtained after reaction for 2 hours. There were sufficient amounts of amplification products obtained after reaction for 1 hour with the primer set 2. Similar tests were conducted with other primer sets.

Figure 10:
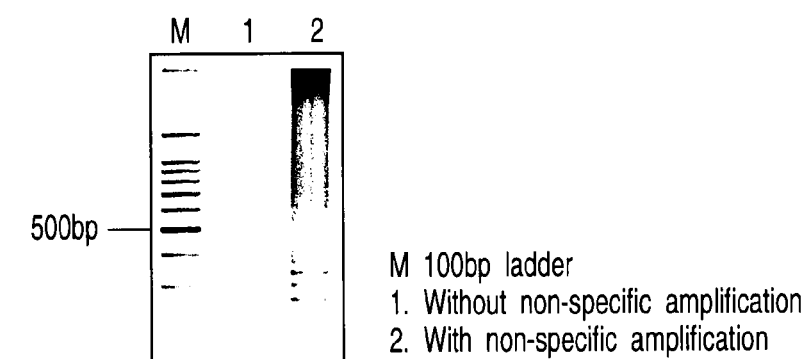
FIG. 10 is an electrophoretogram showing non-specific amplification products.

As a result, the primer sets giving sufficient amounts of amplification products after reaction for 1 hour were the primer sets 2, 3, 4, 5, 7, 8, 12, and 13. The primer sets giving sufficient amounts of amplification products after reaction for 2 hour were the primer sets 1, 2, 3, 4, 5, 6, 7, 8, 12, and 13. There were smaller amounts of or no amplification products obtained with the primer sets 9, 10, 11, and 14. The negative controls of the respective primer sets were also subjected to electrophoresis. As a result, there was non-specific amplification observed with the primer sets 12 and 13. A typical example is shown in FIG. 10.

The results above showed that the primer sets 1, 2, 3, 4, 5, 6, 7, and 8 are preferable, and that the primer sets 2, 3, 4, 5, 7, and 8 are most preferable. The results are summarized in Table 2.

[Test 2: Primer for A1298C]

Amplification was performed at 63° C. for 1 hour or 2 hours, by using 9 kinds of nucleotide primer sets containing MTHFR A1298C polymorphic site in the FP region. The composition of the reaction solution is shown in Table 1. The template DNA used was a human genome. For examination of the presence or absence of contamination and non-specific amplification, a negative control containing sterilized ultra-pure water instead of the human genome was prepared in all sets. After amplification reaction, amplification products were identified by 3% agarose electrophoresis.

The nucleotide primer sets used are shown in Table 3.

The preferable inner primer provided by the present invention is determined by the results above. As apparent to those who are skilled in the art, the most important primer in the LAMP reaction is the inner primer. Although an inner primer is essential in amplification reaction, outer and loop primers are not essential. Addition of outer and loop primers to the amplification reaction solution may lead to an increase in amplification efficiency, but it's positional change gives less influence on amplification efficiency than that of the inner primer. Thus, the outer primers (F3 and B3 primers) can be designed optionally. For example, it is preferably placed in

TABLE 3

Primer set designed to have A1298C in FP and FPc regions

| Primer set | SEQ ID No. | Name | Sequence | 1-hour amplification | 2-hour amplification | Non-specific amplification |
|---|---|---|---|---|---|---|
| 6 | 14 | FIP-1 | CGGTTTGGTTCTCCCGAGAGGGCTGAAGATGTGGGGGGA | X | X | Not-occurred |
|   | 15 | BIP-1 | GTCACAAAGTGAGTGATGCTGGAGTACAGGATGGGGAAGTCACA |   |   |   |
| 1 | 14 | FIP-1 | CGGTTTGGTTCTCCCGAGAGGGCTGAAGATGTGGGGGGA | ○ | ○ | Not-occurred |
|   | 16 | BIP-2 | GTCACAAAGTGAGTGATGCTGGAGTAGCTGGGGTCAGGCC |   |   |   |
| 2 | 14 | FIP-1 | CGGTTTGGTTCTCCCGAGAGGGCTGAAGATGTGGGGGGA | ○ | ○ | Not-occurred |
|   | 17 | BIP-3 | GTGAGTGATGCTGGAGTGGGAGCTGGGGTCAGGCC |   |   |   |
| 7 | 14 | FIP-1 | CGGTTTGGTTCTCCCGAGAGGGCTGAAGATGTGGGGGGA | X | X | Not-occurred |
|   | 18 | BIP-4 | GTGAGTGATGCTGGAGTGGGCCGCAGCCTGGCC |   |   |   |
| 3 | 14 | FIP-1 | CGGTTTGGTTCTCCCGAGAGGGCTGAAGATGTGGGGGGA | X | ○ | Not-occurred |
|   | 19 | BIP-5 | CCCTGGTTCATCCCCTGCCCGCAGCCTGGCC |   |   |   |
| 4 | 14 | FIP-1 | CGGTTTGGTTCTCCCGAGAGGGCTGAAGATGTGGGGGGA | ○ | ○ | Not-occurred |
|   | 20 | BIP-6 | CCCTGGTTCATCCCCTGCGGAAGTCACAGCCCCG |   |   |   |
| 5 | 14 | FIP-1 | CGGTTTGGTTCTCCCGAGAGGGCTGAAGATGTGGGGGGA | ○ | ○ | Not-occurred |
|   | 21 | BIP-7 | AGCTGCAGGCCAGGCTGATGGAGGGGAGGGCAC |   |   |   |
| 8 | 22 | FIP-2 | TGGTTCTCCCGAGAGGTAAAGAACGCTGAAGATGTGGGGGGA | ○ | ○ | Occurred |
|   | 16 | BIP-2 | GTCACAAAGTGAGTGATGCTGGAGTAGCTGGGGTCAGGCC |   |   |   |
| 9 | 23 | FIP-3 | TGGTTCTCCCGAGAGGTAAAGAACGCTGAAGATGTGGGGGGA | ○ | ○ | Occurred |
|   | 17 | BIP-3 | GTGAGTGATGCTGGAGTGGGAGCTGGGGTCAGGCC |   |   |   |
|   | 24 | F3 | GCTGAAGGACTACTACCTCTTCTACC |   |   |   |
|   | 25 | B3-1 | GCACAGGATGGGGAAGTC |   |   |   |
|   | 26 | B3-2 | CTTTGCCATGTCCACAGC |   |   |   |
|   | 28 | LBc | CGGGGCTGTGACTTCC |   |   |   |

The nucleotide of SEQ ID No. 24 was used as the F3 primer in all sets. The nucleotide of SEQ ID No. 25 was used as the B3 primer in primer sets 1, 2, 6, 7, 8, and 9; and the nucleotide of SEQ ID No. 26, in primer sets 4 and 5.

[Test 2: Results]

As a result, the primer sets giving sufficient amounts of amplification products after reaction for 1 hour were the primer sets 1, 2, 4, 5, 8 and 9. The primer sets giving sufficient amounts of amplification products after reaction for 2 hours were the primer sets 1, 2, 3, 4, 5, 8 and 9. There was no amplification product observed with the primer set 6 or 7. There was non-specific amplification observed with the primer sets 8 and 9.

The results above showed that the primer sets 1, 2, 3, 4, and 5 are preferable, and that the primer sets 1, 2, 4, and 5 are most preferable. The results are summarized in Table 3.

the region within 60 bases from the 5' terminal of the F2 region and the region within 60 bases from the 3' terminal of the B2c region. Thus, the F3 region having the same sequence as the F3 primer is preferably placed in the region within 60 bases from the 5' terminal of the F2 region, and the B3c region having a sequence complementary to that of the B3 primer, in the region within 60 bases from the 3' terminal of the B2c region.

The loop primer is preferably designed to bind to a loop other than the loop to which the inner primer binds, and the loop primer is not placed in the inner primer region.

The inner, outer, and loop primers are preferably not placed at the site where mutation may be presented. If a primer has to be designed in the mutation position, it is preferable to introduce a mix base or a universal base such as deoxyinosine (dI) into such position.

<Selection of Nucleotide Probe>

The chain of the nucleotide probe is neither too long nor too short. Generally, an increase in chain length leads to an increase in binding force, although there is some difference according to the kind of base. An excessively small chain length of the nucleotide probe leads to deterioration of the hybridization efficiency between the nucleotide probe and amplification products. Conversely, an excessively large chain length of the nucleotide probe leads to decrease in one-base difference between the wild-type nucleotide probe and the variant nucleotide probe. As a result, non-specific bonding between wild-type amplification products and variant nucleotide probes and also between variant amplification products and wild-type nucleotide probes increases. Thus, it is preferable to use a nucleotide probe having an appropriate chain length, for example of 10 to 35 bases, for detection of a single-nucleotide polymorphism.

The binding force may be indicated by the temperature of dissociation of the double-strand nucleotide, Tm. The Tm value is calculated, for example, by the nearest neighbor method, Wallance method, or GC % method. In the present invention, used is the nearest neighbor method (Breslauer et. al., Proc. Natl. Acad. Sct. USA, Vol. 83, pp. 3746-3750, June 1986; Freier et. al., Proc. Natl. Acad. Sct. USA, Vol. 83, pp. 9373-9377, December 1986; Schildkraut et. al., BIOPOLYMERS, Vol. 3, pp. 195-208, 1965). In the invention, it is calculated under the condition of a $Na^+$ concentration of 50 mM and a nucleotide probe (oligonucleotide) concentration of 0.5 µM.

Hereinafter, a test for selection of a nucleotide probe suitably used in detecting amplification products obtained according to the present invention will be described.

[Test 3-1: Probe for Detection of C677T]

LAMP amplification was performed at 63° C. for 1 hour by using a human genome determined to be heterozygous by PCR-RFLP analysis as the template and also by using the primer set 2 for detection of C677T. The primer set 2 for detection of C677T was the set determined to be the best in the test 1 above. The amplification products obtained were detected on a current-detection DNA chip.

Nucleotide probe:

The nucleotide sequences of the nucleotide probes tested are shown in Table 4. The nucleotide probe used was a minus chain. 3' Terminal of the nucleotide probe was thiol-modified for immobilization on an electrode. The negative control probe was a nucleotide having a sequence completely unrelated to the MTHFR gene sequence.

Support for Nucleotide Probe Immobilization:

Gold electrodes were made on a DNA chip, and a nucleotide probe was immobilized thereon. Immobilization was performed by using the strong bonding force between thiol and gold. A probe solution containing nucleotide probe having a thiol-modified terminal was spotted on the gold electrode, and after 1 hour, the support was immersed in 1 mM mercaptohexanol solution and then, washed with 0.2×SSC solution. The same probe was spotted on two electrodes. After washing, the support was washed with ultrapure water and dried in air, to give a nucleotide probe-immobilized support.

The nucleotide probes were immobilized on the following electrodes respectively:

Electrodes 1-2: negative probe (SEQ ID No. 29)
Electrodes 3-4: wild-type nucleotide probe 15mer (SEQ ID No. 30)
Electrodes 5-6: wild-type nucleotide probe 17mer (SEQ ID No. 31)
Electrodes 7-8: wild-type nucleotide probe 18mer (SEQ ID No. 32)
Electrodes 9-10: wild-type nucleotide probe 19mer (SEQ ID No. 33)
Electrodes 11-12: wild-type nucleotide probe 21mer (SEQ ID No. 34)
Electrodes 13-14: variant nucleotide probe 17mer (SEQ ID No. 35)
Electrodes 15-16: variant nucleotide probe 19mer (SEQ ID No. 36)
Electrodes 17-18: variant nucleotide probe 20mer (SEQ ID No. 37)
Electrodes 19-20: variant nucleotide probe 24mer (SEQ ID No. 38)

Hybridization between amplification products and nucleotide probe and detection thereof:

To the amplification products obtained by amplification were added salts at a final concentration of 2×SSC, and the mixture was allowed to hybridize with the electrode-immobilized nucleotide probe. The reaction temperatures were 35, 45, 50, 55, and 60° C., and the reaction period was 60 minutes. Then, the DNA chip was washed mildly with ultrapure water. The DNA chip was immersed in a phosphate buffer containing 50 µM of an intercalating agent Hoechst 33258 solution for 10 minutes and washed, and then, the oxidative current response of the Hoechst 33258 molecule was measured.

[Test 3-1: Results]

Figure 11:
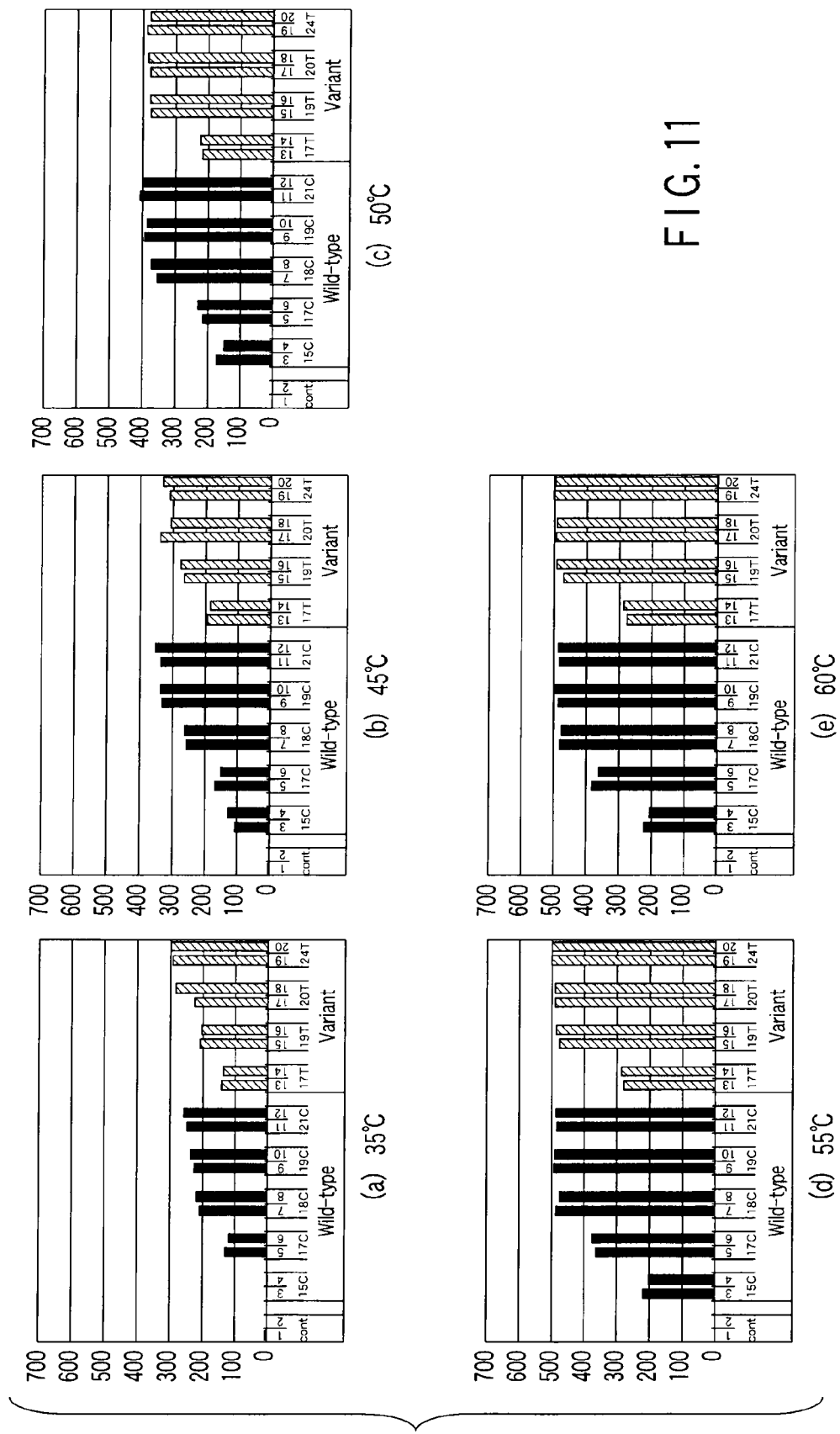
FIG. 11 shows graphs showing test results 1 of a probe for detection of C677T.

Results are summarized in FIG. 11. The signal increased as the reaction temperature increased, indicating that an increase in reaction temperature leads to an increase in

TABLE 4

Nucleotide probe used in detection of products amplified with primer set 2 for detection of C677T

|  | SEQ ID No. | Base number | Tm value | F/R | Sequence |
|---|---|---|---|---|---|
| Negative control | 29 | 14 mer |  |  | GTGCTGCAGGTGCG |
| C677T Wild-type | 30 | 15 mer | 62.1 | R | TGAAATCGGCTCCCG |
|  | 31 | 17 mer | 66.2 | R | ATGAAATCGGCTCCCGC |
|  | 32 | 18 mer | 67.9 | R | GATGAAATCGGCTCCCGC |
|  | 33 | 19 mer | 70.6 | R | GATGAAATCGGCTCCCGCA |
|  | 34 | 21 mer | 73.4 | R | TGATGAAATCGGCTCCCGCAG |
| Variant | 35 | 17 mer | 61.2 | R | ATGAAATCGACTCCCGC |
|  | 36 | 19 mer | 66.2 | R | GATGAAATCGACTCCCGCA |
|  | 37 | 20 mer | 68.9 | R | TGATGAAATCGACTCCCGCA |
|  | 38 | 24 mer | 71.0 | R | ATGATGAAATCGACTCCCGCAGAC | hybridization efficiency. The tests at reaction temperatures 55 and 60° C. gave almost the same results.

[Test 3-2: Probe for Detection of C677T]

Then, hybridization was performed in a similar manner to test 3-1, except that the reaction temperature was 55° C. and the reaction times were 10, 20, 40, 60, and 120 minutes.

[Test 3-2: Results]

Results are summarized in FIG. 12. The tests at reaction times of 10 and 120 minutes gave almost the same results, indicating that the hybridization reaction was already in the saturated state after 10 minutes.

Wild-type nucleotide probes (15C: SEQ ID No. 30 and 17C: SEQ ID No. 31) and a variant nucleotide probe (17T: SEQ ID No. 35) relatively shorter in chain length gave a signal relatively lower in intensity. Wild-type nucleotide probes (18C: SEQ ID No. 32, 19C: SEQ ID No. 33, and 21C: SEQ ID No. 34) and variant nucleotide probes (19T: SEQ ID No. 36, 20T: SEQ ID No. 37, and 24T: SEQ ID No. 38) gave a signal almost the same in intensity.

[Test 3-3: Probe for Detection of C677T]

Then, hybridization was performed in a similar manner to test 3-1, except that the reaction temperature was 55° C. and the reaction time was 20 minutes. Then, the nucleotide probe-immobilized support was washed as immersed for 20 minutes in a 0.2×SSC washing buffer at 40, 45, or 50° C. The analyte nucleotides used for amplification in the present test were 3 kinds of human genomes determined to be wild homozygous, variant homozygous, and heterozygous, respectively, by analyzing with PCR-polymerase chain reaction-restriction fragment length polymorphism (RFLP).

[Test 3-3: Results]

Figure 13A:
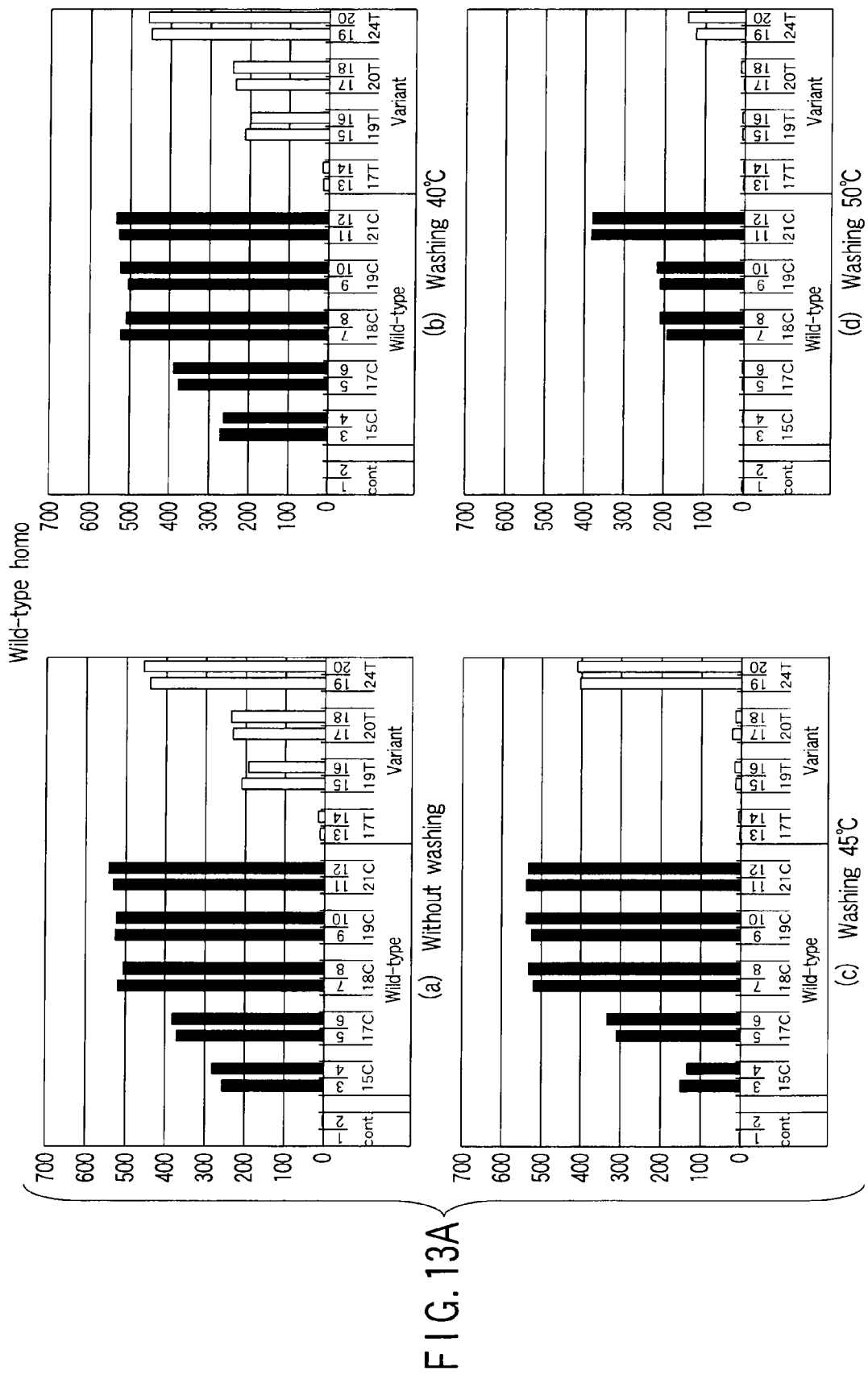
FIG. 13A shows graphs showing test results 3 (wild-type) of a probe for detection of C677T.
Figure 13B:
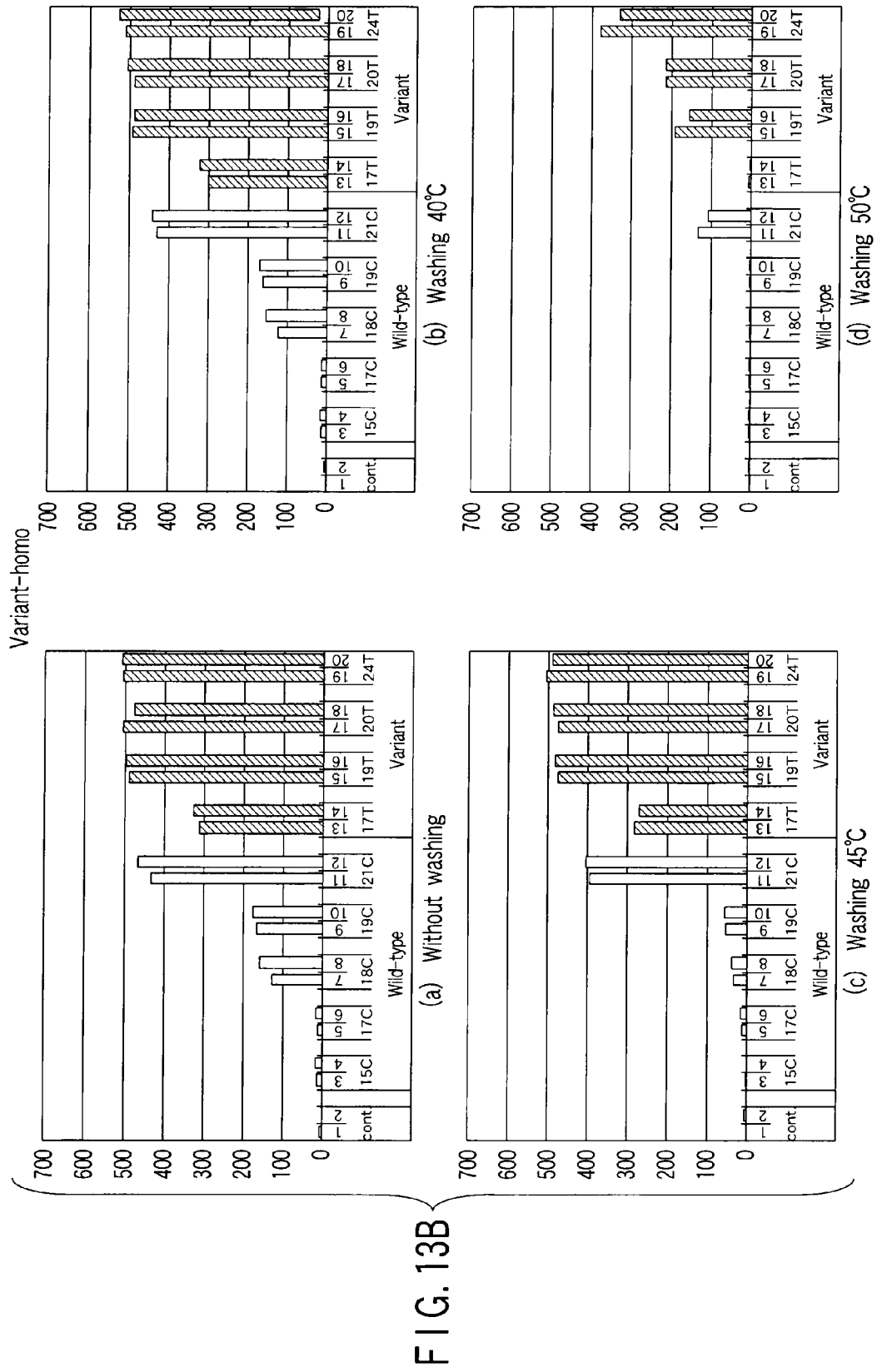
FIG. 13B shows graphs showing test results 3 (variant) of a probe for detection of C677T.
Figure 13C:
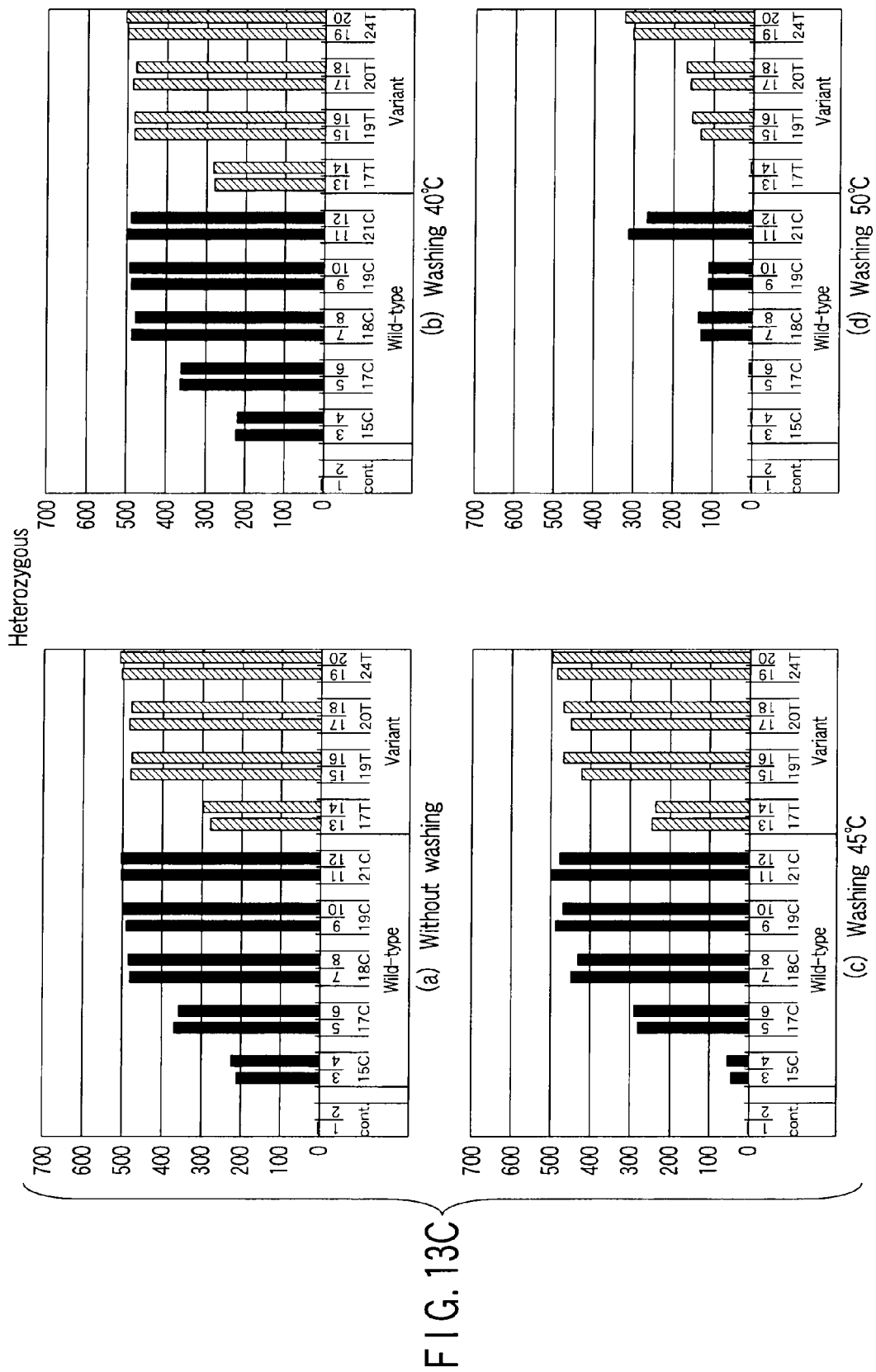
FIG. 13C shows graphs showing test results 3 (heterozygous) of a probe for detection of C677T.

Results are summarized in FIGS. 13A to 13C. When the DNA chip was not washed (only cleaned mildly with ultra-pure water), there were wild-type amplification products detected by the variant nucleotide probe and also variant amplification products detected by the wild-type nucleotide probe, indicating presence of non-specific hybridization. The results at a washing temperature of 40° C. were almost the same as those without washing.

At a washing temperature of 45° C., wild-type amplification products were detected by wild-type nucleotide probes (18C and 19C) at high signal intensity, but almost no signal was detected by variant nucleotide probes (19T and 20T). Similarly, variant amplification products were detected by variant nucleotide probes (19T and 20T) at high signal intensity, but almost no signal was detected by wild-type nucleotide probes (18C and 19C), indicating that bonds formed by non-specific hybridization were broken by washing at 45° C. Heterozygous amplification products were detected both by wild-type nucleotide probes (18C and 19C) and variant nucleotide probes (19T and 20T) at higher signal intensity.

The current detected was lower after washing at 50° C., indicating that amplification products were separated from the nucleotide probe by washing. After washing at 50° C., the signal of wild-type amplification products by wild-type nucleotide probe (21C) decreased, but the signal of the variant amplification products by wild-type nucleotide probe remained high, indicating non-specific binding remaining. Similarly, the signal of the variant amplification product by variant nucleotide probe (24T) decreased, but the signal of wild-type amplification products by variant nucleotide probe remained high.

The results showed that the wild-type nucleotide probes (18C and 19C) and the variant nucleotide probes (19T and 20T) give an ideal detection pattern. Thus, the nucleotide probes most preferably used according to the present invention are wild-type nucleotide probes (18C: SEQ ID No. 32 and 19C: SEQ ID No. 33) and variant nucleotide probes (19T: SEQ ID No. 36 and 20T: SEQ ID No. 37).

The Tm values of the nucleotide probes used in the test are also summarized in Table 4. As apparent from Table 4, the nucleotide probes preferably used in the present invention are wild-type nucleotide probes having a Tm value of 62 to 73° C., preferably 68 to 71° C., and variant nucleotide probes having a Tm value of 61 to 71° C., preferably 66 to 69° C.

[Test 4-1: Probe for Detection of A1298C]

LAMP amplification was performed at 63° C. for 1 hour, by using a human genome determined to be heterozygous by sequence analysis as the template and also the primer set 5 for detection of A1298C. The primer set 5 for detection of A1298C is the set determined to be the best primer in the test 1 above. The amplification products obtained were detected on a current-detection DNA chip.

Nucleotide Probe:

The nucleotide sequences of the nucleotide probes tested are summarized in Table 5. The nucleotide probe used was a minus chain. 3' Terminal of the nucleotide probe was thiol-modified for immobilization on an electrode. The negative control probe was a nucleotide having a sequence completely unrelated to the MTHFR gene sequence.

TABLE 5

Nucleotide probe used in detection of products amplified with primer set 5 for detection of A1298C

|                    | SEQ ID No. | Base number | Tm value | F/R | Sequence |
|--------------------|------------|-------------|----------|-----|----------|
| A1298C Wild-type   | 39         | 25 mer      | 64.4     | R   | TTCAAAGACACTTTCTTCACTGGTC |
|                    | 40         | 27 mer      | 67.3     | R   | CTTCAAAGACACTTTCTTCACTGGTCA |
|                    | 41         | 29 mer      | 68.2     | R   | ACTTCAAAGACACTTTCTTCACTGGTCAG |
|                    | 42         | 32 mer      | 72.0     | R   | GACTTCAAAGACACTTTCTTCACTGCTCAGCT |
| Variant            | 43         | 22 mer      | 63.2     | R   | CAAAGACACTTGCTTCACTGGT |
|                    | 44         | 24 mer      | 66.5     | F   | TCAAAGACACTTGCTTCACTGGTC |
|                    | 45         | 25 mer      | 67.4     | R   | TTCAAAGACACTTGCTTCACTGGTC |
|                    | 46         | 26 mer      | 69.6     | R   | TTCAAAGACACTTGCTTCACTGGTCA |
|                    | 47         | 29 mer      | 72.8     | R   | CTTCAAAGACACTTGCTTCACTGGTCAGC |

Nucleotide probe-immobilized support

Nucleotide probe-immobilized supports were prepared, in a similar manner to test 3-1.

The nucleotide probes were immobilized on the following electrodes respectively:

Electrodes 1-2: negative probe (SEQ ID No. 29)
Electrodes 3-4: wild-type nucleotide probe 25mer (SEQ ID No. 39)
Electrodes 5-6: wild-type nucleotide probe 27mer (SEQ ID No. 40)
Electrodes 7-8: wild-type nucleotide probe 29mer (SEQ ID No. 41)
Electrodes 9-10: wild-type nucleotide probe 32mer (SEQ ID No. 42)
Electrodes 11-12: variant nucleotide probe 22mer (SEQ ID No. 43)
Electrodes 13-14: variant nucleotide probe 24mer (SEQ ID No. 44)
Electrodes 15-16: variant nucleotide probe 25mer (SEQ ID No. 45)
Electrodes 17-18: variant nucleotide probe 26mer (SEQ ID No. 46)
Electrodes 19-20: variant nucleotide probe 29mer (SEQ ID No. 47)

Hybridization between amplification products and nucleotide probe and detection thereof:

To the amplification products obtained by amplification were added salts at a final concentration of 2×SSC, and the mixture was allowed to hybridize with the electrode-immobilized nucleotide probe. The reaction temperatures were 35, 45, 50, 55, and 60° C., and the reaction period was 60 minutes. Then, the DNA chip was washed mildly with ultrapure water. The DNA chip was immersed in a phosphate buffer containing 50 µM of an intercalating agent Hoechst 33258 solution for 10 minutes and washed, and then, the oxidative current response of the Hoechst 33258 molecule was measured.

[Test 4-1: Results]

Results are summarized in FIG. 14. The signal increased as the reaction temperature increased, indicating that an increase in reaction temperature leads to an increase in hybridization efficiency. The tests at reaction temperatures 55 and 60° C. gave almost the same results.

[Test 4-2: Probe for Detection of A1298C]

Then, hybridization was performed in a similar manner to test 4-1, except that the reaction temperature was 55° C. and the reaction time was 20 minutes. Then, the nucleotide probe-immobilized support was washed as immersed in a 0.2×SSC washing buffer at 45° C. for 20 minutes. The analyte nucleotides used for amplification in the present test were 3 kinds of human genomes determined to be wild homozygous, variant homozygous, and heterozygous respectively, by sequence analysis.

[Test 4-2: Results]

Figure 15:
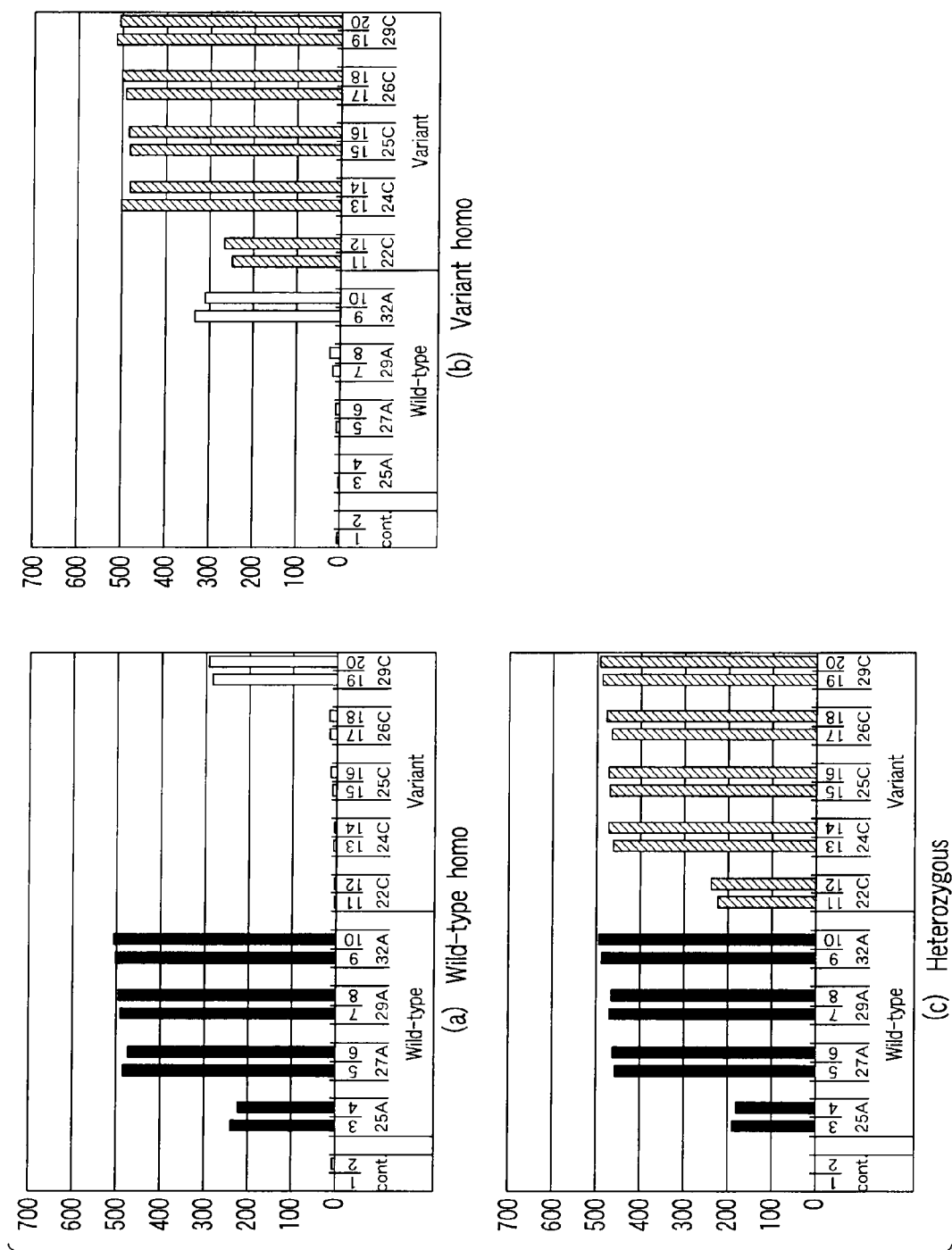
FIG. 15 shows graphs showing test results 2 of a probe for detection of A1298C.

Results are summarized in FIG. 15. Wild-type amplification products were detected by wild-type nucleotide probes (27A and 29A) at high signal intensity, while almost no signal was detected by the variant nucleotide probes (24C, 25C, and 26C). Similarly, variant amplification products were detected by variant nucleotide probes (24C, 25C, and 26C) at high signal intensity, while almost no signal was detected by the wild-type nucleotide probes (27A and 29A). Heterozygous amplification products were detected both by the wild-type nucleotide probes (27A and 29A) and the variant nucleotide probes (24C, 25C, and 26C) at high signal intensity.

The results showed that the wild-type nucleotide probes (27A and 29A) and the variant nucleotide probes (24C, 25C, and 26C) give an ideal detection pattern. Thus, the nucleotide probes used most preferably according to the present invention are the wild-type nucleotide probes (27A: SEQ ID No. 40 and 29A: SEQ ID No. 41) and the variant nucleotide probes (24C: SEQ ID No. 44, 25C: SEQ ID No. 45, and 26C: SEQ ID No. 46). The detection results are summarized in Table 5.

The Tm values of the nucleotide probes used were also summarized in Table 5. As apparent from Table 5, the nucleotide probes preferably used in the present invention are wild-type nucleotide probes having a Tm value of 64 to 72° C., preferably 67 to 68° C., and variant nucleotide probes having a Tm value of 63 to 73° C., preferably 67 to 70° C.

<Analyte Sample>

The analyte sample subjected to the present invention is not particularly limited, and may be, for example, human blood, serum, leukocyte, hair root, or oral mucous membranes. Nucleotide components are extracted from the analyte sample, to give a sample solution subjected to the test for detecting a target nucleotide. The extraction method is not particularly limited and, for example, a commercially available nucleotide extraction tool such as QIAamp (manufactured by QIAGEN) or Sumai test (manufactured by Sumitomo Metal Industries Ltd.) may be used.

<Kit>

Another aspect of the present invention provides a kit including the above-described primer set for the LAMP method for use in the detection method according to the present invention. The kit may optionally contain, for example, a chain-substituting DNA polymerase, a synthesis substrate, and a buffer solution.

In another aspect, the present invention provides a nucleotide probe for detection of the amplification products amplified with the primer set according to the invention. The present invention also provides a nucleotide probe-immobilized support on which the nucleotide probe according to the invention was immobilized. The probe-immobilized support is provided preferably as a DNA chip or DNA microarray.

The kit according to the invention can also include the nucleotide probe or the nucleotide probe-immobilized support additionally.

In another aspect, the present invention provides a method of detecting single-nucleotide polymorphisms C677T and A1298C of MTHFR simultaneously. In the present aspect, C677T and A1298C are amplified as described above, separately, and then, the amplification products are mixed, to prepare a liquid mixture. The liquid mixture is subjected to the detection as described above. In the present aspect, it is possible to detect the genotypes of C677T and A1298C simultaneously.

EXAMPLE

[Shortening of Amplification Period by Introduction of Loop Primer]

A LBc loop primer of SEQ ID No. 27 (see Table 2) was added to the nucleotide primer set 2 for detection of C677T, and a LBc loop primer of SEQ ID No. 28 (see Table 3) to the nucleotide primer set 5 for detection of A1298C, respectively in 25 µl reaction solution in an amount of 40 pmol, and the mixture was amplified. As a result, the saturation amplification period was shortened from 60 minutes to about 30 minutes.

[Simultaneous Detection of C677T and A1298C]

A test of simultaneous detection of C677T and A1298C was performed. A human genome sample was amplified at 63° C. for 1 hour, by using the nucleotide primer set 2 for detection of C677T or the nucleotide primer set 5 for detection of A1298C, respectively. The human genomes were three kinds of human genomes determined to be wild homozygous, variant homozygous, and heterozygous respectively by PCR-RFLP analysis or sequence analysis. After amplification reaction, two kinds of amplification products respectively obtained from C677T and A1298C were mixed, to prepare a mixed reaction solution.

Nucleotide Probe:

The mixed reaction solution was subjected to detection using nucleotide probes for C677T and nucleotide probes for A1298C. The nucleotide probes were as follows:

C677T: wild-type nucleotide probe (SEQ ID No. 32), and variant nucleotide probe (SEQ ID No. 37), A1298C: wild-type nucleotide probe (SEQ ID No. 40), and variant nucleotide probe (SEQ ID No. 45).

All the nucleotide probes were minus chain, and 3' terminal of the nucleotide probe was thiol-modified.

Preparation of probe nucleotide-immobilized electrode:

A probe nucleotide-immobilized electrode was prepared in a manner similar to the method described in test 3-1 above.

The nucleotide probes were immobilized on the following electrodes respectively:

Electrodes 1-2: negative probe (SEQ ID No. 29)

Electrodes 3-4: C677T wild-type nucleotide probe 26mer (SEQ ID No. 32)

Electrodes 5-6: C677T variant nucleotide probe 27mer (SEQ ID No. 37)

Electrodes 7-8: A1298C wild-type nucleotide probe 23mer (SEQ ID No. 40)

Electrodes 9-10: A1298C variant nucleotide probe 26mer (SEQ ID No. 45)

Hybridization between amplification products and nucleotide probe and detection thereof:

The test was performed in a similar manner to the test 3-2.

[Results]

Figure 16:
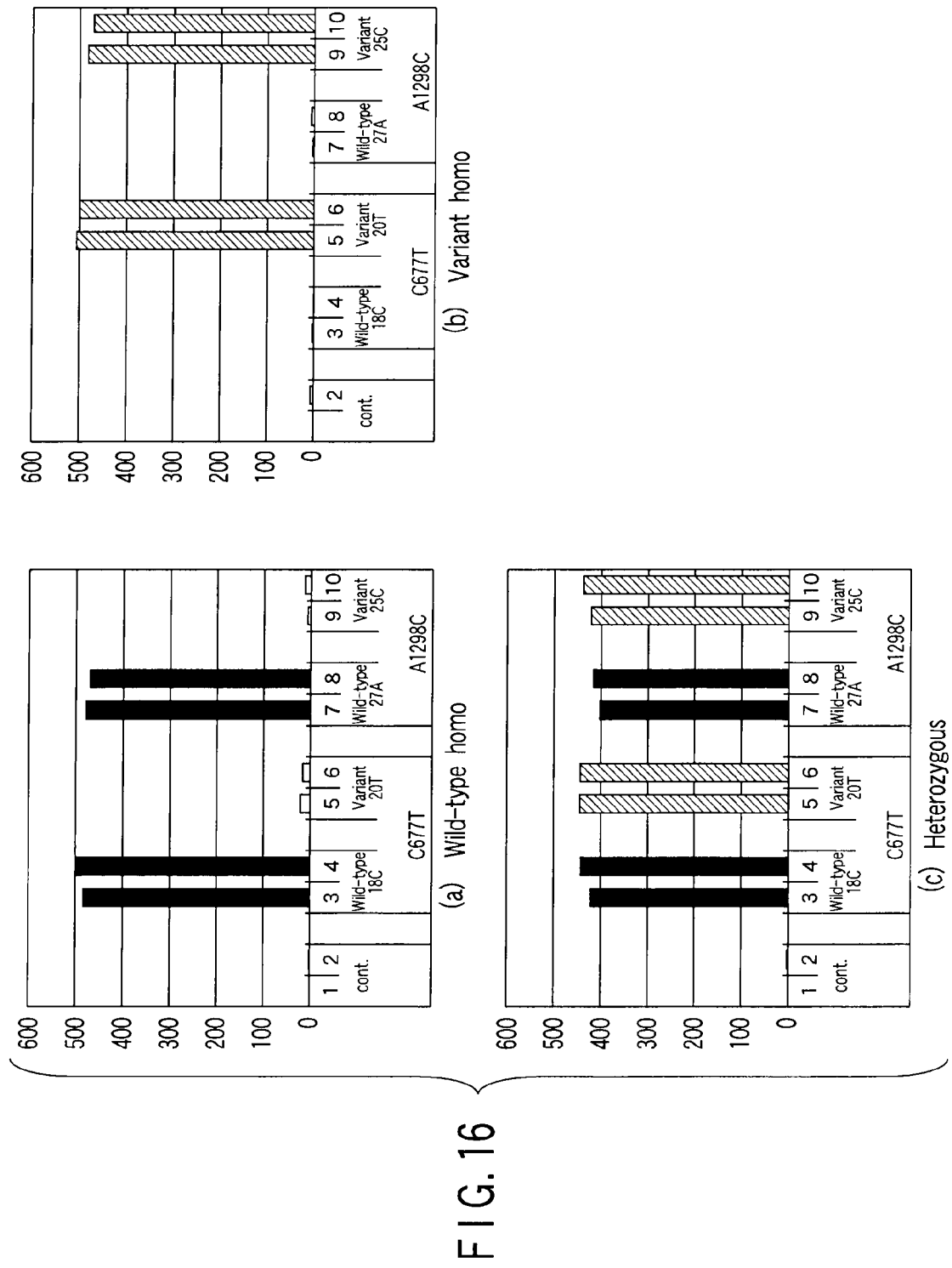
FIG. 16 shows graphs showing the results of simultaneous detection of C677T and A1298C.

Results are summarized in FIG. 16. An ideal detection pattern was observed both for C677T and A1298C. The results showed that it was possible to detect C677T and A1298C simultaneously by using a DNA chip according to the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as

What is claimed is:

1. A nucleotide primer set for LAMP amplification, used for detecting a genotype of a single-nucleotide polymorphism C677T of an MTHFR gene, wherein
when a target nucleotide sequence has F3 region, F2 region and F1 region in turn from a 5' terminal and B3c region, B2c region and B1c region in turn from a 3' terminal, and
when a primer set comprises an FIP primer having a sequence identical with that of the F2 region in a 3' terminal side and a sequence complementary to the F1 region in a 5' terminal side, an F3 primer having a sequence identical with that of the F3 region, a BIP primer having a sequence complementary to the B2c region in a 3' terminal side and a sequence identical with that of the B1c region in a 5' terminal side, and a B3 primer having a sequence complementary to the B3c region,
the primer set comprises:
an FIP and BIP primer set selected from the group consisting of: SEQ ID NO: 1 and SEQ ID NO: 3; SEQ ID NO: 1 and SEQ ID NO: 4; SEQ ID NO: 1 and SEQ ID NO: 5; SEQ ID NO: 1 and SEQ ID NO: 6; SEQ ID NO: 1 and SEQ ID NO: 7; SEQ ID NO: 9 and SEQ ID NO: 3; SEQ ID NO: 9 and SEQ ID NO: 4; and SEQ ID NO: 9 and SEQ ID NO: 5;
an F3 primer binding to a region within 60 bases from the 5' terminal of a F2c region of a complementary nucleotide sequence of the target nucleotide sequence, wherein the F2c region is complementary to the F2 region; and
a B3 primer binding to a region within 60 bases from the 3' terminal of the B2c region of the target nucleotide sequence.

2. The nucleotide primer set according to claim 1, wherein the F1P and B1P primer set is selected from the group consisting of: SEQ ID NO: 1 and SEQ ID NO: 4; SEQ ID NO: 1 and SEQ ID NO: 5; SEQ ID NO: 1 and SEQ ID NO: 6; SEQ ID NO: 1 and SEQ ID NO: 7; SEQ ID NO: 9 and SEQ ID NO: 4; and SEQ ID NO: 9 and SEQ ID NO: 5.

3. The nucleotide primer set according to claim 1, wherein the F1P and B1P primer set is SEQ ID NO: 1 and SEQ ID NO: 4.

4. A nucleotide primer set for LAMP amplification, used for detecting a genotype of a single-nucleotide polymorphism A1298C of an MTHFR gene, wherein
when a target nucleotide sequence has F3 region, F2 region and F1 region in turn from a 5' terminal and B3c region, B2c region and B1c region in turn from a 3' terminal, and
when a primer set comprises an FIP primer having a sequence identical with that of the F2 region in a 3' terminal side and a sequence complementary to the F1 region in a 5' terminal side, an F3 primer having a sequence identical with that of the F3 region, a B1P primer having a sequence complementary to the B2c region in a 3' terminal side and a sequence identical with that of the B1c region in a 5' terminal side, and a B3 primer having a sequence complementary to the B3c region,
the primer set comprises:
an F1P and B1P primer set selected from the group consisting of: SEQ ID NO: 14 and SEQ ID NO: 16; SEQ ID NO: 14 and SEQ ID NO: 17; SEQ ID NO: 14 and SEQ ID NO: 19; SEQ ID NO: 14 and SEQ ID NO: 20; and SEQ ID NO: 14 and SEQ ID NO: 21;
an F3 primer binding to a region within 60 bases from the 5' terminal of a F2c region of a complementary nucleotide sequence of the target nucleotide sequence, wherein the F2c region is complementary to the F2 region; and
a B3 primer binding to a region within 60 bases from the 3' terminal of the B2c region of the target nucleotide sequence.

5. The nucleotide primer set according to claim 4, wherein the F1P and B1P primer set is selected from the group consisting of: SEQ ID NO: 14 and SEQ ID NO: 16; SEQ ID NO: 14 and SEQ ID NO: 17; SEQ ID NO: 14 and SEQ ID NO: 20; and SEQ ID NO: 14 and SEQ ID NO: 21.

6. The nucleotide primer set according to claim 4, wherein the F1P and B1P primer set is SEQ ID NO: 14 and SEQ ID NO: 21.

7. The nucleotide primer set according to claim 1, wherein:
the F3 primer has a sequence of SEQ ID No. 10; and
the B3 primer has a sequence of SEQ ID No. 11, when the F1P and B1P primer set is selected from the group consisting of: SEQ ID NO: 1 and SEQ ID NO: 3; and SEQ ID NO: 9 and SEQ ID NO: 3; or a sequence of SEQ ID No. 12, when the F1P and B1P primer set is selected from the group consisting of: SEQ ID NO: 1 and SEQ ID NO: 4; SEQ ID NO: 1 and SEQ ID NO: 5; SEQ ID NO: 1 and SEQ ID NO: 6; SEQ ID NO: 1 and SEQ ID NO: 7; SEQ ID NO: 9 and SEQ ID NO: 4; and SEQ ID NO: 9 and SEQ ID NO: 5.

8. A kit for detecting a genotype of a single-nucleotide polymorphism C677T of the MTHFR gene, comprising the primer set according to claim 1, a wild-type nucleotide probe and a variant nucleotide probe,
wherein:
the wild-type nucleotide probe is complementary to a wild-type amplification product and has a Tm value of 62 to 73° C., and the single-nucleotide polymorphism C677T site is located three bases or more inside from the both terminal the wild-type nucleotide probe, and
the variant nucleotide probe is complementary to a variant amplification product and has a Tm value of 61 to 71° C., and the single-nucleotide polymorphism C677T site is located three bases or more inside from the both terminal the variant nucleotide probe.

9. The kit according to claim 8, wherein the wild-type nucleotide probe has a sequence of SEQ ID No. 32 or 33 or a sequence complementary thereto, and the variant nucleotide probe has a sequence of SEQ ID No. 36 or 37 or a sequence complementary thereto.

10. The kit according to claim 8, wherein the probes are immobilized on a support.

11. The kit according to claim 8, wherein:
the F3 primer has a sequence of SEQ ID No. 10; and
the B3 primer has a sequence of SEQ ID No. 11, when the F1P and B1P primer set is selected from the group consisting of: SEQ ID NO: 1 and SEQ ID NO: 3; and SEQ ID NO: 9 and SEQ ID NO: 3; or a sequence of SEQ ID No. 12, when the F1P and B1P primer set is selected from the group consisting of: SEQ ID NO: 1 and SEQ ID NO: 4; SEQ ID NO: 1 and SEQ ID NO: 5; SEQ ID NO: 1 and SEQ ID NO: 6; SEQ ID NO: 1 and SEQ ID NO: 7; SEQ ID NO: 9 and SEQ ID NO: 4; and SEQ ID NO: 9 and SEQ ID NO: 5.

12. The nucleotide primer set according to claim 4, wherein:
an F3 primer has a sequence of SEQ ID No. 24 and,
a B3 primer has a sequence of SEQ ID No. 25, when the F1P and B1P primer set is selected from the group consisting of: SEQ ID NO: 14 and SEQ ID NO: 16; and SEQ ID NO: 14 and SEQ ID NO: 17; or a sequence of SEQ ID No. 26, when the F1P and B1P primer set is selected from the group consisting of: SEQ ID NO: 14 and SEQ ID NO: 20; and SEQ ID NO: 14 and SEQ ID NO: 21.

13. A kit for detecting a genotype of a single-nucleotide polymorphism A1298C of the MTHFR gene, comprising the primer set according to claim 4, a wild-type nucleotide probe and a variant nucleotide probe,
wherein:
the wild-type nucleotide probe is complementary to a wild-type amplification product and has a Tm value of 64 to 72° C., and the single-nucleotide polymorphism A1298C site is located three bases or more inside from the both terminal the wild-type nucleotide probe, and
the variant nucleotide probe is complementary to a variant amplification product and has a Tm value of 63 to 73° C., and the single-nucleotide polymorphism A1298C site is located three bases or more inside from the both terminal the variant nucleotide probe.

14. The kit according to claim 13, wherein the wild-type nucleotide probe has a sequence of SEQ ID No. 40 or 41 or a sequence complementary thereto, and the variant nucleotide probe has a sequence of SEQ ID No. 44 or 45 or a sequence complementary thereto.

15. The kit according to claim 13, wherein the probes are immobilized on a support.

16. The kit according to claim 13, wherein;
the F3 primer has a sequence of SEQ ID No. 24 and,
the B3 primer has a sequence of SEQ ID No. 25, when the F1P and B1P primer set is selected from the group consisting of: SEQ ID NO: 14 and SEQ ID NO: 16; and SEQ ID NO: 14 and SEQ ID NO: 17; or a sequence of SEQ ID No. 26, when the F1P and B1P primer set is selected from the group consisting of: SEQ ID NO: 14 and SEQ ID NO: 20; and SEQ ID NO: 14 and SEQ ID NO: 21.

* * * * *

```
                       SEQUENCE LISTING

<160> NUMBER OF SEQ ID NOS: 47

<210> SEQ ID NO 1
<211> LENGTH: 38
<212> TYPE: DNA
<213> ORGANISM: Artificial sequence
<220> FEATURE:
<223> OTHER INFORMATION: C677T Primer FIP-1

<400> SEQUENCE: 1
tcagcctcaa agaaaagctg aggctgacct gaagcact                         38

<210> SEQ ID NO 2
<211> LENGTH: 41
<212> TYPE: DNA
<213> ORGANISM: Artificial sequence
<220> FEATURE:
<223> OTHER INFORMATION: C677T Primer BIP-1

<400> SEQUENCE: 2
cttccgcttt gtgaaggcat gcccctcacc tggatgggaa a                     41

<210> SEQ ID NO 3
<211> LENGTH: 43
<212> TYPE: DNA
<213> ORGANISM: Artificial sequence
<220> FEATURE:
<223> OTHER INFORMATION: C677T Primer BIP-2

<400> SEQUENCE: 3
cacattcttc cgctttgtga aggcccctca cctggatggg aaa                   43

<210> SEQ ID NO 4
<211> LENGTH: 40
<212> TYPE: DNA
<213> ORGANISM: Artificial sequence
```

```
<220> FEATURE:
<223> OTHER INFORMATION: C677T Primer BIP-3

<400> SEQUENCE: 4
caggagagcc cataagctcc cttcagcact ccacccagag                40

<210> SEQ ID NO 5
<211> LENGTH: 40
<212> TYPE: DNA
<213> ORGANISM: Artificial sequence
<220> FEATURE:
<223> OTHER INFORMATION: C677T Primer BIP-4

<400> SEQUENCE: 5
gagagcccat aagctccctc catcagcact ccacccagag                40

<210> SEQ ID NO 6
<211> LENGTH: 40
<212> TYPE: DNA
<213> ORGANISM: Artificial sequence
<220> FEATURE:
<223> OTHER INFORMATION: C677T Primer BIP-5

<400> SEQUENCE: 6
gagagcccat aagctccctc caactcagca ctccacccag                40

<210> SEQ ID NO 7
<211> LENGTH: 39
<212> TYPE: DNA
<213> ORGANISM: Artificial sequence
<220> FEATURE:
<223> OTHER INFORMATION: C677T Primer BIP-6

<400> SEQUENCE: 7
agcccataag ctccctccac cactcagcac tccacccag                 39

<210> SEQ ID NO 8
<211> LENGTH: 34
<212> TYPE: DNA
<213> ORGANISM: Artificial sequence
<220> FEATURE:
<223> OTHER INFORMATION: C677T Primer BIP-7

<400> SEQUENCE: 8
ccatcgtccc cgggaggagc ttatgggctc tcct                      34

<210> SEQ ID NO 9
<211> LENGTH: 42
<212> TYPE: DNA
<213> ORGANISM: Artificial sequence
<220> FEATURE:
<223> OTHER INFORMATION: C677T Primer FIP-2

<400> SEQUENCE: 9
gcctcaaaga aaagctgcgt gtgaagcact tgaaggagaa gg             42

<210> SEQ ID NO 10
<211> LENGTH: 18
<212> TYPE: DNA
<213> ORGANISM: Artificial sequence
<220> FEATURE:
<223> OTHER INFORMATION: C677T Primer F3

<400> SEQUENCE: 10
gttaccccaa aggccacc                                         18
```

<210> SEQ ID NO 11
<211> LENGTH: 19
<212> TYPE: DNA
<213> ORGANISM: Artificial sequence
<220> FEATURE:
<223> OTHER INFORMATION: C677T Primer B3-1

<400> SEQUENCE: 11
ggagcttatg ggctctcct					19

<210> SEQ ID NO 12
<211> LENGTH: 19
<212> TYPE: DNA
<213> ORGANISM: Artificial sequence
<220> FEATURE:
<223> OTHER INFORMATION: C677T Primer B3-2

<400> SEQUENCE: 12
tctgggaaga actcagcga					19

<210> SEQ ID NO 13
<211> LENGTH: 18
<212> TYPE: DNA
<213> ORGANISM: Artificial sequence
<220> FEATURE:
<223> OTHER INFORMATION: C677T Primer B3-3

<400> SEQUENCE: 13
tcagcactcc acccagag					18

<210> SEQ ID NO 14
<211> LENGTH: 39
<212> TYPE: DNA
<213> ORGANISM: Artificial sequence
<220> FEATURE:
<223> OTHER INFORMATION: A1298C Primer FIP-1

<400> SEQUENCE: 14
cggtttggtt ctcccgagag ggctgaagat gtggggga					39

<210> SEQ ID NO 15
<211> LENGTH: 44
<212> TYPE: DNA
<213> ORGANISM: Artificial sequence
<220> FEATURE:
<223> OTHER INFORMATION: A1298C Primer BIP-1

<400> SEQUENCE: 15
gtcacaaagt gagtgatgct ggagtacagg atggggaagt caca					44

<210> SEQ ID NO 16
<211> LENGTH: 40
<212> TYPE: DNA
<213> ORGANISM: Artificial sequence
<220> FEATURE:
<223> OTHER INFORMATION: A1298C Primer BIP-2

<400> SEQUENCE: 16
gtcacaaagt gagtgatgct ggagtagctg gggtcaggcc					40

<210> SEQ ID NO 17
<211> LENGTH: 35
<212> TYPE: DNA
<213> ORGANISM: Artificial sequence
<220> FEATURE:
<223> OTHER INFORMATION: A1298C Primer BIP-3

<400> SEQUENCE: 17
gtgagtgatg ctggagtggg agctggggtc aggcc                35

<210> SEQ ID NO 18
<211> LENGTH: 33
<212> TYPE: DNA
<213> ORGANISM: Artificial sequence
<220> FEATURE:
<223> OTHER INFORMATION: A1298C Primer BIP-4

<400> SEQUENCE: 18
gtgagtgatg ctggagtggg ccgcagcctg gcc                  33

<210> SEQ ID NO 19
<211> LENGTH: 31
<212> TYPE: DNA
<213> ORGANISM: Artificial sequence
<220> FEATURE:
<223> OTHER INFORMATION: A1298C Primer BIP-5

<400> SEQUENCE: 19
ccctggttca tccccctgccc gcagcctggc c                   31

<210> SEQ ID NO 20
<211> LENGTH: 34
<212> TYPE: DNA
<213> ORGANISM: Artificial sequence
<220> FEATURE:
<223> OTHER INFORMATION: A1298C Primer BIP-6

<400> SEQUENCE: 20
ccctggttca tccccctgcgg aagtcacagc cccg                34

<210> SEQ ID NO 21
<211> LENGTH: 33
<212> TYPE: DNA
<213> ORGANISM: Artificial sequence
<220> FEATURE:
<223> OTHER INFORMATION: A1298C Primer BIP-7

<400> SEQUENCE: 21
agctgcaggc caggctgatg gaggggaggg cac                  33

<210> SEQ ID NO 22
<211> LENGTH: 42
<212> TYPE: DNA
<213> ORGANISM: Artificial sequence
<220> FEATURE:
<223> OTHER INFORMATION: A1298C Primer FIP-2

<400> SEQUENCE: 22
tggttctccc gagaggtaaa gaacgctgaa gatgtggggg ga        42

<210> SEQ ID NO 23
<211> LENGTH: 42
<212> TYPE: DNA
<213> ORGANISM: Artificial sequence
<220> FEATURE:
<223> OTHER INFORMATION: A1298C Primer FIP-3

<400> SEQUENCE: 23
tggttctccc gagaggtaaa gaacgctgaa gatgtggggg ga        42

```
<210> SEQ ID NO 24
<211> LENGTH: 26
<212> TYPE: DNA
<213> ORGANISM: Artificial sequence
<220> FEATURE:
<223> OTHER INFORMATION: A1298C Primer F3

<400> SEQUENCE: 24
gctgaaggac tactacctct tctacc                                      26

<210> SEQ ID NO 25
<211> LENGTH: 18
<212> TYPE: DNA
<213> ORGANISM: Artificial sequence
<220> FEATURE:
<223> OTHER INFORMATION: A1298C Primer B3-1

<400> SEQUENCE: 25
gcacaggatg gggaagtc                                               18

<210> SEQ ID NO 26
<211> LENGTH: 18
<212> TYPE: DNA
<213> ORGANISM: Artificial sequence
<220> FEATURE:
<223> OTHER INFORMATION: A1298C Primer B3-2

<400> SEQUENCE: 26
ctttgccatg tccacagc                                               18

<210> SEQ ID NO 27
<211> LENGTH: 21
<212> TYPE: DNA
<213> ORGANISM: Artificial sequence
<220> FEATURE:
<223> OTHER INFORMATION: C677T Primer LBc

<400> SEQUENCE: 27
ccgcaccgtc ctcgcacagg c                                           21

<210> SEQ ID NO 28
<211> LENGTH: 16
<212> TYPE: DNA
<213> ORGANISM: Artificial sequence
<220> FEATURE:
<223> OTHER INFORMATION: A1298C Primer LBc

<400> SEQUENCE: 28
cggggctgtg acttcc                                                 16

<210> SEQ ID NO 29
<211> LENGTH: 14
<212> TYPE: DNA
<213> ORGANISM: Artificial sequence
<220> FEATURE:
<223> OTHER INFORMATION: Negative Controle Probe

<400> SEQUENCE: 29
gtgctgcagg tgcg                                                   14

<210> SEQ ID NO 30
<211> LENGTH: 15
<212> TYPE: DNA
<213> ORGANISM: Artificial sequence
<220> FEATURE:
<223> OTHER INFORMATION: C677T Wild Type Probe
```

```
<400> SEQUENCE: 30
tgaaatcggc tcccg                                                      15

<210> SEQ ID NO 31
<211> LENGTH: 17
<212> TYPE: DNA
<213> ORGANISM: Artificial sequence
<220> FEATURE:
<223> OTHER INFORMATION: C677T Wild Type Probe

<400> SEQUENCE: 31
atgaaatcgg ctcccgc                                                    17

<210> SEQ ID NO 32
<211> LENGTH: 18
<212> TYPE: DNA
<213> ORGANISM: Artificial sequence
<220> FEATURE:
<223> OTHER INFORMATION: C677T Wild Type Probe

<400> SEQUENCE: 32
gatgaaatcg gctcccgc                                                   18

<210> SEQ ID NO 33
<211> LENGTH: 19
<212> TYPE: DNA
<213> ORGANISM: Artificial sequence
<220> FEATURE:
<223> OTHER INFORMATION: C677T Wild Type Probe

<400> SEQUENCE: 33
gatgaaatcg gctcccgca                                                  19

<210> SEQ ID NO 34
<211> LENGTH: 21
<212> TYPE: DNA
<213> ORGANISM: Artificial sequence
<220> FEATURE:
<223> OTHER INFORMATION: C677T Wild Type Probe

<400> SEQUENCE: 34
tgatgaaatc ggctcccgca g                                               21

<210> SEQ ID NO 35
<211> LENGTH: 17
<212> TYPE: DNA
<213> ORGANISM: Artificial sequence
<220> FEATURE:
<223> OTHER INFORMATION: C677T Mutation Type Probe

<400> SEQUENCE: 35
atgaaatcga ctcccgc                                                    17

<210> SEQ ID NO 36
<211> LENGTH: 19
<212> TYPE: DNA
<213> ORGANISM: Artificial sequence
<220> FEATURE:
<223> OTHER INFORMATION: C677T Mutation Type Probe

<400> SEQUENCE: 36
gatgaaatcg actcccgca                                                  19
```

<210> SEQ ID NO 37
<211> LENGTH: 20
<212> TYPE: DNA
<213> ORGANISM: Artificial sequence
<220> FEATURE:
<223> OTHER INFORMATION: C677T Mutation Type Probe

<400> SEQUENCE: 37
tgatgaaatc gactcccgca                                              20

<210> SEQ ID NO 38
<211> LENGTH: 24
<212> TYPE: DNA
<213> ORGANISM: Artificial sequence
<220> FEATURE:
<223> OTHER INFORMATION: C677T Mutation Type Probe

<400> SEQUENCE: 38
atgatgaaat cgactcccgc agac                                         24

<210> SEQ ID NO 39
<211> LENGTH: 25
<212> TYPE: DNA
<213> ORGANISM: Artificial sequence
<220> FEATURE:
<223> OTHER INFORMATION: A1298C Wild Type Probe

<400> SEQUENCE: 39
ttcaaagaca ctttcttcac tggtc                                        25

<210> SEQ ID NO 40
<211> LENGTH: 27
<212> TYPE: DNA
<213> ORGANISM: Artificial sequence
<220> FEATURE:
<223> OTHER INFORMATION: A1298C Wild Type Probe

<400> SEQUENCE: 40
cttcaaagac actttcttca ctggtca                                      27

<210> SEQ ID NO 41
<211> LENGTH: 29
<212> TYPE: DNA
<213> ORGANISM: Artificial sequence
<220> FEATURE:
<223> OTHER INFORMATION: A1298C Wild Type Probe

<400> SEQUENCE: 41
acttcaaaga cactttcttc actggtcag                                    29

<210> SEQ ID NO 42
<211> LENGTH: 32
<212> TYPE: DNA
<213> ORGANISM: Artificial sequence
<220> FEATURE:
<223> OTHER INFORMATION: A1298C Wild Type Probe

<400> SEQUENCE: 42
gacttcaaag acactttctt cactggtcag ct                                32

<210> SEQ ID NO 43
<211> LENGTH: 22
<212> TYPE: DNA
<213> ORGANISM: Artificial sequence
<220> FEATURE:
<223> OTHER INFORMATION: A1298C Mutation Type Probe -continued

```
<400> SEQUENCE: 43
caaagacact tgcttcactg gt                                                22

<210> SEQ ID NO 44
<211> LENGTH: 24
<212> TYPE: DNA
<213> ORGANISM: Artificial sequence
<220> FEATURE:
<223> OTHER INFORMATION: A1298C Mutation Type Probe

<400> SEQUENCE: 44
tcaaagacac ttgcttcact ggtc                                              24

<210> SEQ ID NO 45
<211> LENGTH: 25
<212> TYPE: DNA
<213> ORGANISM: Artificial sequence
<220> FEATURE:
<223> OTHER INFORMATION: A1298C Mutation Type Probe

<400> SEQUENCE: 45
ttcaaagaca cttgcttcac tggtc                                             25

<210> SEQ ID NO 46
<211> LENGTH: 26
<212> TYPE: DNA
<213> ORGANISM: Artificial sequence
<220> FEATURE:
<223> OTHER INFORMATION: A1298C Mutation Type Probe

<400> SEQUENCE: 46
ttcaaagaca cttgcttcac tggtca                                            26

<210> SEQ ID NO 47
<211> LENGTH: 29
<212> TYPE: DNA
<213> ORGANISM: Artificial sequence
<220> FEATURE:
<223> OTHER INFORMATION: A1298C Mutation Type Probe

<400> SEQUENCE: 47
cttcaaagac acttgcttca ctggtcagc                                         29
```